(12) United States Patent
Joabsson et al.

(10) Patent No.: US 8,546,326 B2
(45) Date of Patent: Oct. 1, 2013

(54) GLP-1 ANALOGUE FORMULATIONS

(75) Inventors: Fredrik Joabsson, Lund (SE); Markus Johnsson, Lund (SE); Fredrik Tiberg, Lund (SE)

(73) Assignee: Camurus AB (SE)

( * ) Notice: Subject to any disclaimer, the term of this patent is extended or adjusted under 35 U.S.C. 154(b) by 1155 days.

(21) Appl. No.: 11/908,740

(22) PCT Filed: Jun. 6, 2006

(86) PCT No.: PCT/GB2006/002079
§ 371 (c)(1),
(2), (4) Date: Feb. 13, 2008

(87) PCT Pub. No.: WO2006/131730
PCT Pub. Date: Dec. 14, 2006

(65) Prior Publication Data
US 2008/0146490 A1    Jun. 19, 2008

(30) Foreign Application Priority Data

Jun. 6, 2005  (WO) ............... PCT/GB2005/002217
Dec. 9, 2005  (WO) ............... PCT/GB2005/004752

(51) Int. Cl.
*A61K 38/26*   (2006.01)
*A61K 49/00*   (2006.01)
*A61K 9/127*   (2006.01)

(52) U.S. Cl.
USPC ........... 514/7.2; 424/9.2; 424/283.1; 530/308

(58) Field of Classification Search
None
See application file for complete search history.

(56) References Cited

U.S. PATENT DOCUMENTS

| | | | |
|---|---|---|---|
| 4,938,763 A | 7/1990 | Dunn et al. | |
| 5,340,802 A | 8/1994 | Shiosaki et al. | |
| 5,480,656 A | 1/1996 | Okada et al. | |
| 5,531,925 A | 7/1996 | Landh et al. | |
| 5,639,480 A | 6/1997 | Bodmer et al. | |
| 5,776,885 A | 7/1998 | Orsolini et al. | |
| 5,807,573 A * | 9/1998 | Ljusberg-Wahren et al. | 424/450 |
| 5,955,502 A | 9/1999 | Hansen et al. | |
| 6,066,328 A | 5/2000 | Ribier et al. | |
| 6,113,943 A * | 9/2000 | Okada et al. ................. | 424/457 |
| 6,228,383 B1 | 5/2001 | Hansen et al. | |
| 6,458,924 B2 * | 10/2002 | Knudsen et al. ............. | 530/324 |
| 6,464,987 B1 | 10/2002 | Fanara et al. | |
| 8,097,239 B2 * | 1/2012 | Johnsson et al. ............. | 424/9.2 |
| 8,182,834 B2 | 5/2012 | Johnsson et al. | |
| 8,187,629 B2 | 5/2012 | Barauskas et al. | |
| 8,236,292 B2 | 8/2012 | Thuresson et al. | |
| 8,236,755 B2 | 8/2012 | Thuresson et al. | |
| 2002/0026027 A1 | 2/2002 | Ansell | |
| 2003/0022242 A1 | 1/2003 | Anderson | |
| 2004/0018241 A1 | 1/2004 | Houze et al. | |
| 2004/0201117 A1 | 10/2004 | Anderson | |
| 2005/0136059 A1 | 6/2005 | Thorpe et al. | |
| 2006/0073203 A1 | 4/2006 | Ljusberg-Wahren et al. | |
| 2007/0080323 A1 | 4/2007 | Joabsson et al. | |
| 2007/0110777 A1 | 5/2007 | Joabsson et al. | |
| 2007/0134336 A1 | 6/2007 | Worle et al. | |
| 2007/0231374 A1 | 10/2007 | Tiberg et al. | |
| 2008/0124394 A1 | 5/2008 | Johnsson et al. | |
| 2008/0161276 A1 | 7/2008 | Johnsson et al. | |
| 2008/0214995 A1 | 9/2008 | Boyd et al. | |
| 2008/0274176 A1 | 11/2008 | Johnsson et al. | |
| 2009/0069221 A1 | 3/2009 | Joabsson et al. | |
| 2009/0155193 A1 | 6/2009 | Joabsson et al. | |
| 2009/0170782 A1 | 7/2009 | Joabsson et al. | |
| 2010/0210519 A1 | 8/2010 | Johnsson et al. | |
| 2011/0230569 A1 | 9/2011 | Nistor et al. | |
| 2012/0028890 A1 | 2/2012 | Nistor et al. | |
| 2012/0269772 A1 | 10/2012 | Thuresson et al. | |

FOREIGN PATENT DOCUMENTS

| | | |
|---|---|---|
| DK | WO 03/002136 A | 1/2003 |
| EP | 1 600 162 A1 | 11/2005 |
| WO | WO 93/06921 A1 | 4/1993 |
| WO | WO 95/34287 A1 | 12/1995 |
| WO | WO 97/13528 A1 | 4/1997 |
| WO | WO 98/47487 A1 | 10/1998 |
| WO | WO 02/02716 A2 | 1/2002 |
| WO | WO 02/066014 A2 | 8/2002 |
| WO | WO 02/068561 A2 | 9/2002 |
| WO | WO 02/068562 A2 | 9/2002 |
| WO | 03 057235 A2 | 7/2003 |
| WO | WO 2004/087215 A1 | 10/2004 |
| WO | WO 2005/014162 A1 | 2/2005 |
| WO | WO 2005/021022 A | 3/2005 |

(Continued)

OTHER PUBLICATIONS

Wermuth, Pure and Appl. Chem, 1998, 70, 1129-1143.*
Martel et al., "Enzyme Linked Immunosorbent Assay (ELISA) Method for the Determination of TH0318, a New GLP-1 Analogue in Development for Diabetes," presented at the 2005 AAPS Annual Meeting and Exposition, Abstract No. W5008.
Loughrey et al., "Development of a Sensitive Sandwich ELISA for Detecting Full Length Biologically Active TH0318, a GLP-1 Analogue," presented at the 2005 AAPS Annual Meeting and Exposition, Abstract No. W5009.
MSDS for Ethylene Glycol and Abbreviations used in Toxicity data, Nov. 23, 2009.

(Continued)

*Primary Examiner* — Satyanarayana R Gudibande
(74) *Attorney, Agent, or Firm* — J. A. Lindeman & Co., PLLC

(57) ABSTRACT

The present invention relates to compositions forming a low viscosity mixture of: a) at least one neutral diacyl lipid, such as a diacyl glycerol; b) at least one phospholipid, such as a phosphatidyl choline; c) at least one biotolerable solvent, such as an oxygen containing solvent; d) at least one GLP-1 analogue; wherein the pre-formulation forms, or is capable of forming, at least one liquid crystalline phase structure upon contact with an aqueous fluid. The invention further relates to methods of treatment comprising administration of such compositions, especially in treating diabetes, and to pre-filled administration devices and kits containing the formulations.

15 Claims, 1 Drawing Sheet

(56) References Cited

FOREIGN PATENT DOCUMENTS

| WO | WO 2005/046642 A | 5/2005 |
|---|---|---|
| WO | 2005 048952 A2 | 6/2005 |
| WO | WO 2005/063213 A1 | 7/2005 |
| WO | WO 2005/070394 A | 8/2005 |
| WO | WO 2005/117830 | 12/2005 |
| WO | WO 2006/075123 A1 | 7/2006 |
| WO | WO 2006/075124 A1 | 7/2006 |
| WO | WO 2006/075125 A1 | 7/2006 |
| WO | WO 2006/077362 A1 | 7/2006 |
| WO | WO 2006/131730 A1 | 12/2006 |
| WO | WO 2008/152401 A1 | 12/2008 |
| WO | WO 2009/024795 A1 | 2/2009 |
| WO | WO 2009/024797 A1 | 2/2009 |
| WO | WO 2010/020794 A1 | 2/2010 |

OTHER PUBLICATIONS

N. Ardjomand et al., "Expression of Somatostatin Receptors in uveal melanomas," Inv. Opthalmol. & Vis. Sci., 2003, vol. 44, No. 3, pp. 980-987.

Barauskas et al., Pharmaceutical Nanotechnology, "Interactions of lipid-based liquid crystalline nanoparticles with model and cell membranes," International Journal of Pharmaceutics 391 (2010) pp. 284-291.

R. Berges, "Eligard: Pharmacokinetics, Effect on Testosterone and PSA Levels and Tolerability," European Urology Supplements, 2005, vol. 4, pp. 20-25.

P. Chanson et al., "Comparison of octreotide acetate LAR and lanreptide SR in patients with acromegaly," Clin. Endocrinology, 2001, vol. 54, No. 1, pp. 11-13, (Abstract only).

Comets et al., "Non parametric analysis of the absorption profile of octreotide in rabbits from long-acting release formulation OncoLAR," J. Controlled Release 59:197-205 (1999).

Definition of analog from http://cancerweb.ncl.ac.uk!omd/about.html, pp. 1-5. Accessed Jul. 7, 2005.

B. L. Erstad, "Octreotide for acute variceal bleeding," Ann. Pharmacother., 2001, vol. 35, No. 5, pp. 618-626. (Abstract only).

A. K. Flogstad et al., "Sandostatin LAR in acromegalic patients: long term treatment," J. Clinical Endocrinology & Metabolism, 1997, vol. 82, No. 1, pp. 23-28.

P. R. Gibson & J. G. Muir, "Reinforcing the mucus: a new therapeutic approach for ulcerative colitis," Gut, 2005, vol. 54, pp. 900-903.

L. M. Grant & F. Tibert, "Normal and Lateral Forces between Lipid Covered Solids in Solution: Correlation with Layer Packing and Structure," Biophysical Journal, 2002, vol. 82, pp. 1373-1385.

B.A. Hills, "Surface-active phospholipid: a Pandora's box of clinical applications. Part II. Barrier and lubricating properties," Internal Medicine Journal, 2002, vol. 32, pp. 242-251.

G. G. Holz et al., "Glucagon-Like Peptide-1 Synthetic Analogs: New Therapeutic Agents for Use in the Treatment of Diabetes Mellitus," Current Medicinal Chemistry (2003), vol. 10, pp. 2471-2483.

H. Hui et al., "Structure and function studies of glucagon-like peptide-1 (GLP-1): the designing of a novel pharmacological agent for the treatment of diabetes," Diabetes Metabolism Research and Reviews, (2005), vol. 21, pp. 313-331.

Invitrogen, "Pluronic F-127," Molecular Probes Invitrogen Detection Technologies, pp. 1-2, 2008.

Johnsson et al., "Physicochemical and Drug Delivery Aspects of Lipid-Based Liquid Crystalline Nanoparticles: A Case Study of Intravenously Administered Propofol," Journal of Nanoscience and Nanotechnology, vol. 6, No. 9/10, pp. 3017-3024, 2006.

Kamo, et al., "Nonlamellar Liquid Crystalline Phases and Their Particle Formation in the Egg Yolk Phosphatidylcholine/Diolein System," Langmuir, vol. 19, pp. 9191-9195, Published on Web Oct. 1, 2003.

Kesisoglou, et al., "Liposomal Formulations of Inflammatory Bowel Disease Drugs: Local versus Systemic Drug Delivery in a Rat Model," Pharmaceutical Research, vol. 22, No. 8, Aug. 2005, pp. 1320-1329.

J. G. M. Klijn et al., "Combined tamoxifen and luteinizing hormone-releasing hormone (LHRH) agonist versus LHRH agonist alone in premenopausal advanced breast cancer: A meta-analysis of four randomized trials," Journal of Clinical Oncology, 2001, vol. 19, No. 2, pp. 343-353 (Abstract only).

L. M. Knudsen, "Glucagon-like Peptide-1: The Basis of a New Class of Treatment for Type 2 Diabetes," J. Med. Chem. (2004), vol. 47, pp. 4128-4134.

L. M. Knudsen et al., "Potent Derivatives of Glucagon-like Peptide-1 with Pharmacokinetic Properties Suitable for Once Daily Administration," J. Med. Chem. (2000) vol. 43, pp. 1664-1669.

I. Lancranjan et al., "Sandostatin LAR: Pharmacokinetics. Pharmacodynamics, Efficacy and Tolerability in Acromegalic Patients," Metabolism, 1995, vol. 44, No. 1, pp. 18-26.

"Leutinizing Hormone Releasing Hormone (LHRH) Agonists: Goserelin (Zoladex) vs. Leuprolide (Lupron) for Prostate Cancer," DoD Pharmacoeconomic Center Update, Newsletter, Dec. 2000, vol. 1, No. 1, print out from http://www.pec.ha.osd.mil.com, pp. 1-3.

O. Sartor "Eligard: Leuprolide Acetate in a Novel Sustained-Release Delivery System," Urology, 2003, vol. 61, (Supplement 2A), pp. 25-31.

K. J. Schuh et al., "Onset, magnitude and duration of opioid blockade produced by buprenorphine and naltrexone in humans," Psychopharmacology, (Berl), 1999 Jul., vol. 145, No. 2, pp. 162-174 (Abstract only).

J. C. Shah et al., "Cubic phase gels as drug delivery systems," Advanced Drug Delivery Reviews, 2001, vol. 47, pp. 229-250.

W. Stremmel et al., "Retarded release phosphatidylcholine benefits patients with chronic active ulcerative colitis," Gut, 2005, vol. 54, pp. 966-971.

A Sturm & A. U. Dignass, "Modulation of gastrointestinal wound repair and inflammation by phospholipids," Biochimica et Biophysica Acta, 2002, vol. 1582, pp. 282-288.

Tiberg et al., "Drug delivery applications of non-lamellar liquid crystalline phases and nanoparticles", J. Drug Del Sci. Tech., 21(1) pp. 101-109, 2011.

Tiberg et al., "Treatment Of Oral Mucositis Pain By A Bioadhesive Barrier Forming Lipid Solution," Support Care Center 17(7):918 (2009) (attached hereto as Annex 4 to Evidentiary Declaration Under 37 C.F.R. § 1.132 of Fredrik Tiberg).

Welin et al., "High-dose treatment with a long-acting somatostatin analogue in patients with advanced midgut carcinoid tumours," 2004, Society of the European Journal of Endocrinology, vol. 151, pp. 107-112.

E. Woltering et al., "Octreotide acetate (LAR) dose effect on plasma octreotide levels: Impact on neuroendocrine tumor Management," F. Clin Oncology, 2005 ASCO Annual Meeting Proceedings, vol. 23, No. 16S, pp. 3177 (Abstract only).

E. A. Woltering, "A discussion on the utility of various routes of administration of octreotide acetate," from http://www.carcinoid.org/medpro/docs/WoltPump2005.htm.

International Search Report of PCT/GB2005/004745 dated May 8, 2006.

International Preliminary Report on Patentability of PCT/GB2005/004745 dated Jul. 20, 2007.

Written Opinion of PCT/GB2005/004745 dated May 8, 2006.

International Search Report of PCT/GB2005/04748 dated Mar. 23, 2006.

International Preliminary Report on Patentability of PCT/GB2005/04748 dated Mar. 12, 2007.

Written Opinion of PCT/GB2005/04748 dated Mar. 23, 2006.

International Search Report of PCT/GB2005/04752 dated Mar. 17, 2006.

International Preliminary Report on Patentability of PCT/GB2005/04752 dated Mar. 12, 2007.

Written Opinion of PCT/GB2005/04752 dated Mar. 17, 2006.

International Search Report of PCT/GB2005/004746 dated Mar. 16, 2006.

International Preliminary Report on Patentability and Written Opinion of PCT/GB2005/004746 dated Jul. 17, 2007.

International Search Report of PCT/GB2006/002079 dated Aug. 25, 2006.
International Preliminary Report on Patentability and Written Opinion of PCT/GB2006/002079 dated Dec. 6, 2007.
International Search Report of PCT/GB2008/002035 dated Oct. 6, 2008.
International Preliminary Report on Patentability of PCT/GB2008/002035 Dec. 17, 2009.
Written Opinion of PCT/GB2008/002035 dated Oct. 6, 2008.
International Search Report of PCT/GB2008/002857 dated Jan. 28, 2009.
International Preliminary Report on Patentability and Written Opinion of PCT/GB2008/002857 dated Feb. 24, 2010.
International Search Report of PCT/GB2009/002054 dated Nov. 30, 2009.
International Preliminary Report on Patentability and Written Opinion of PCT/GB2009/002054 dated Feb. 22, 2011.
Office Action in U.S. Appl. No. 11/795,243 dated May 12, 2011.
Office Action in U.S. Appl. No. 11/795,243 dated Mar. 22, 2012.
Office Action in U.S. Appl. No. 11/795,249 dated Jul. 19, 2011.
Office Action in U.S. Appl. No. 11/795,249 dated Oct. 25, 2010.
Office Action in U.S. Appl. No. 11/795,250 dated Dec. 21, 2012.
Office Action in U.S. Appl. No. 11/795,250 dated Mar. 18, 2011.
Office Action in U.S. Appl. No. 11/795,250 dated Jun. 24, 2010.
Office Action in U.S. Appl. No. 11/795,242 dated Jan. 10, 2013.
Office Action in U.S. Appl. No. 11/795,242 dated Dec. 23, 2011.
Office Action in U.S. Appl. No. 11/877,935 dated Dec. 21, 2010.

* cited by examiner

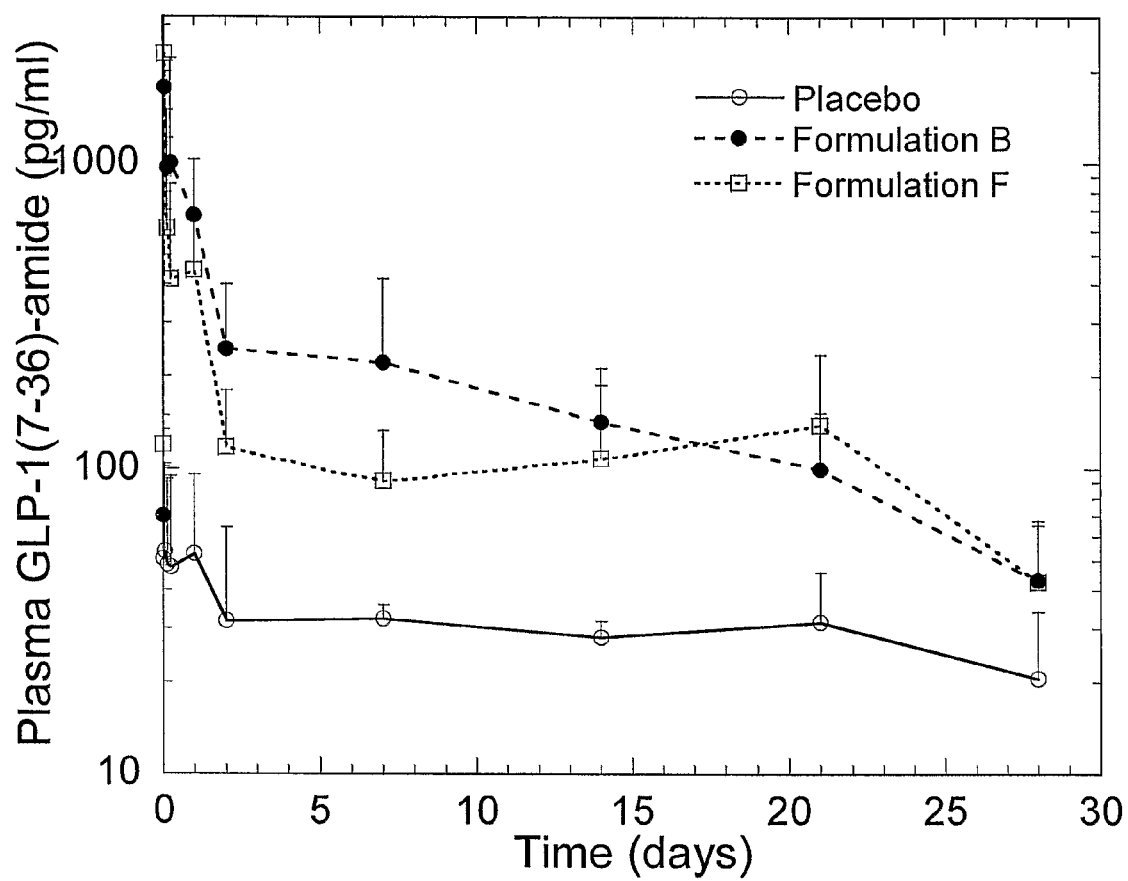

GLP-1 ANALOGUE FORMULATIONS

SEQUENCE LISTING

The instant application contains a Sequence Listing which has been submitted in ASCII format via EFS-Web and is hereby incorporated by reference in its entirety. The ASCII copy, created on Mar. 11, 2011, is named 110005US.txt and is 2,058 bytes in size.

The present invention relates to formulation precursors (pre-formulations) for the in situ generation compositions for the controlled release of active agents such as Glucagon-like-peptide-1 (GLP-1) and/or analogues thereof, and methods of treatment with such formulations. In particular, the invention relates to pre-formulations of amphiphilic components and at least one GLP-1 or analogous active agent for parenteral application, which undergo phase transition upon exposure to aqueous fluids, such as body fluids, thereby forming a controlled release matrix.

Many bioactive agents including pharmaceuticals, nutrients, vitamins and so forth have a "functional window". That is to say that there is a range of concentrations over which these agents can be observed to provide some biological effect. Where the concentration in the appropriate part of the body (e.g. locally or as demonstrated by serum concentration) falls below a certain level, no beneficial effect can be attributed to the agent. Similarly, there is generally an upper concentration level above which no further benefit is derived by increasing the concentration. In some cases increasing the concentration above a particular level results in undesirable or even dangerous effects.

Some bioactive agents have a long biological half-life and/or a wide functional window and thus may be administered occasionally, maintaining a functional biological concentration over a substantial period of time (e.g. 6 hours to several days). In other cases the rate of clearance is high and/or the functional window is narrow and thus to maintain a biological concentration within this window regular (or even continuous) doses of a small amount are required. This can be particularly difficult where non-oral routes of administration (e.g. parenteral administration) are desirable or necessary, since self-administration may be difficult and thus cause inconvenience and/or poor compliance. In such cases it would be advantageous for a single administration to provide active agent at a therapeutic level over the whole period during which activity is needed.

Glucagon-like peptide (GLP)-1 is a potent glucoregulatory hormone that is released from intestinal L cells into the circulation in response to nutrient ingestion and neural and endocrine stimuli. Structurally, GLP-1 is a 37-amino acid peptide with a MW of 4.2 KDa, having a sequence highly conserved between different species. GLP-1 is involved in modification of glucose homeostasis through actions that include potentiation of glucose-stimulated insulin secretion and biosynthesis and suppression of glucagon secretion, gastric emptying, and food intake. The abilities of GLP-1 to stimulate insulin secretion and inhibit glucagon release are glucose-dependent; thus, the risk of hypoglycemia with GLP-1 administration is low. GLP-1 also increases beta-cell mass in preclinical models of diabetes through mechanisms that include stimulation of beta-cell proliferation and neogenesis and inhibition of beta-cell apoptosis. Studies in both animals and humans indicate that GLP-1 may also play a protective role in the cardiovascular system.

The combined actions of GLP-1 have generated substantial interest in using this peptide as a therapeutic agent for the treatment of type 2 diabetes. However, the therapeutic potential of native GLP-1 is limited by its very short plasma half-life (below 2 minutes). This is due to both rapid inactivation by the proteolytic enzyme dipeptidyl peptidase (DPP)-IV and renal clearance. Consequently, long-acting, DPP-IV-resistant GLP-1 analogs have been developed for clinical use, including exenatide (Byetta, Amylin-Lilly), liraglutide (Novo Nordisk), CJC-1131 (ConjuChem), AVE010 (Zealand Pharma—Sanofi-Aventis), LY548806 (Lilly), and TH-0318 (TheraTechnologies). All these are once- or twice-daily administration products; a controlled-release (one week) exenatide product (Exenatide LAR Alkermes-Amylin-Lilly) is currently under clinical investigation. These GLP-1 mimetics bind to GLP-1 receptors with similar affinity and produce biological actions identical to those of native GLP-1 but are resistant to DPP-IV-mediated inactivation and renal clearance. These compounds are able to exert more sustained GLP-1-like activity for longer periods of time in vivo. An alternative therapeutic approach for prolonging the action of native GLP-1 is to inhibit DPP-IV activity, thereby preventing GLP-1 degradation. Several orally active agents that inhibit DPP-IV activity are also being evaluated for the treatment of type 2 diabetes.

The structures and sequences of GLP-1 and some known analogues are shown below starting with two equipotent naturally occurring forms. A straightforward system is used to describe fragments and analogues of GLP-1. For example, $Arg^{34}$-GLP-1(7-37) designates an analogue of GLP-1 formally derived from GLP-1 by deleting the amino acid residues Nos. 1 to 6 and substituting the naturally occurring amino acid residue in position 34 (Lys) by Arg.

Native (human) GLP-1(7-37):

```
                                          (SEQ ID NO: 1)
His⁷-Ala-Glu-Gly¹⁰-Thr-Phe-Thr-Ser-Asp¹⁵-Val-Ser-

Ser-Tyr-Leu²⁰-Glu-Gly-Gln-Ala-Ala²⁵-Lys-Glu-Phe-

Ile-Ala³⁰-Trp-Leu-Val-Lys-Gly-Arg-Gly³⁷
```

Native (human):
GLP-1(7-36)amide (SEQ ID NO: 2)
NovoNordisk (Liraglutide)
$Arg^{34}Lys^{26}$-(N-ε-(γ-Glu(N-α-hexadecanoyl)))-GLP-1(7-37)
Conjuchem (CJC-1131)
$D-Ala^{8}Lys^{37}$-(2-(2-(2-maleimidopropionamido(ethoxy)ethoxy)acetamide))-GLP-1(7-37)
Sanofi-Aventis/Zealand (AVE-010 (ZP10))

```
                                          (SEQ ID NO: 3)
His-Gly-Glu-Gly-Thr-Phe-Thr-Ser-Asp-Leu-Ser-Lys-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Ser-Lys-Lys-Lys-Lys-Lys-Lys
```

Eli Lilly (Exenatide)

```
                                          (SEQ ID NO: 4)
His⁷-Gly-Glu-Gly¹⁰-Thr-Phe-Thr-Ser-Asp¹⁵-Leu-Ser-

Lys-Gln-Met²⁰-Glu-Glu-Glu-Ala-Val²⁵-Arg-Leu-Phe-

Ile-Glu³⁰-Trp-Leu-Lys-Asn-Gly-Gly-Pro³⁷-Ser-Ser-

Gly-Ala-Pro-Pro-Pro-Ser
```

As used herein, "native GLP-1" indicates human GLP-1 (7-37) and/or human GLP-1(7-36)amide and the terms "Liraglutide", "CJC-1131", "AVE-010", and "exenatide" are used to indicate the respective actives above, including their physiologically acceptable salts, esters and derivatives where context allows.

With regard to administration, conditions such as type-2 diabetes are ongoing, and any treatment regime will typically involve long-term, ongoing therapy, for periods of months or years. Currently available GLP-1 therapies are typically injectables which require administration around twice a day for the period of treatment. This will generally be by patient self-administration. Since frequent injection over a long period is not an optimal administration strategy, there is clearly scope for GLP-1 users to benefit from long-acting, sustained formulations, which might be administered much less frequently.

The only long-acting GLP-1 product known to be in development is Exenatide LAR, developed by a collaboration of Alkermes, Amylin and Lilly. This uses the Alkermes Medisorb® delivery system consisting of microspheres of biodegradable polymers. The release system comprises a poly(DL-lactide) (PDLL) polymer microsphere formulation suspended in water, which entraps the GLP-1 analogue exenatide.

Polymer microsphere formulations must generally be administered by means of a sizable needle, typically of 20-gauge or wider. This is necessary as a result of the nature of the polymeric dosing systems used, which are typically polymer suspensions. Evidently, it would be an advantage to provide a system of low viscosity, such as a homogeneous solution, dispersion of fine particles, or $L_2$ phase, which could be administered easily through a narrow needle, thus decreasing the discomfort of the patient during the procedure. In the case of type-2 diabetes, this ease of administration is particularly significant because most patients will currently be on a self-administration regime. Providing a sustained formulation with a duration of a few days, but which is sufficiently complex to administer that it requires treatment by a health-care professional will not be an advantage to all patients over twice-daily self-administration, and is likely to be more costly. Providing a formulation which gives sufficiently long duration to justify a visit to a health professional for administration and/or a preparation which can be self-administered, and reducing preparation time of health-care professionals or patients prior to the actual administration are all important issues.

The poly-lactate, poly-glycolate and poly-lactate-co-glycolate polymers typically used for degrading slow-release formulations, and which are used in the only known GLP-1 sustained release product, are also the cause of some irritation in at least some patients. In particular, these polymers typically contain a certain proportion of acetic acid impurity, which will irritate the injection site on administration. When the polymer then breaks down, lactic acid and glycolic acid are the degradation products so that further irritation is caused. As a result of the combined effects of wide-needle administration and irritant contents, the discomfort at the site of administration and the formation of connective scar tissue are greater than desirable.

From a drug delivery point of view, polymer depot compositions generally have the disadvantage of accepting only relatively low drug loads and having a "burst/lag" release profile. The nature of the polymeric matrix, especially when applied as a solution or pre-polymer, causes an initial burst of drug release when the composition is first administered. This is followed by a period of low release, while the degradation of the matrix begins, followed finally by an increase in the release rate to the desired sustained profile. This burst/lag release profile can cause the in vivo concentration of active agent to burst above the functional window immediately following administration, and then drop back through the bottom of the functional window during the lag period before reaching a sustained functional concentration for a period of time. Evidently, from a functional and toxicological point of view this burst/lag release profile is undesirable and could be dangerous. It may also limit the equilibrium concentration which can be provided due to the danger of adverse effects at the "peak" point. The presence of a lag phase may furthermore require supplementary dosing with repeat injections during the start-up period of depot treatment in order to maintain a therapeutic dose while the concentrations of active provided from the depot are sub-functional.

Evidently, in the case of GLP-1 analogues, it is important that the "burst" period, immediately after administration, is not so pronounced that it causes hypoglycaemia in the subject. GLP-1 is much safer in this respect than insulin, but clinical trials of some GLP-1 analogues have shown hypoglycemic effects with non-sustained release formulations, and the dose injected when a formulation is designed to last for several weeks will be correspondingly higher. It would therefore be a considerable advantage to minimise the immediate "burst" effect upon administration of a GLP-1 analogue composition.

The manufacture of PLGA microbeads and suspensions is additionally a considerable difficulty with certain existing depot systems. In particular, since the beads are particulate, and polymers clog membranes, they cannot generally be sterile-filtered and furthermore, since the PLGA copolymer melts at around 40° C., they cannot be heat-treated for sterility. As a result, a complex manufacturing process must all be conducted under conditions of high sterility.

Further issues with biodegradable polymer microspheres include complex reconstitution prior to injection and limited storage stability, due both to aggregation and degradation of the delivery system and/or active.

The present inventors have now established that by providing a pre-formulation comprising certain amphiphilic components, at least one GLP-1 analogue, and a biologically tolerable solvent in a low viscosity phase, such as molecular solution, a pre-formulation may be generated addressing many of the shortfalls of known depot formulations, and which may be applied to provide a GLP-1 analogue depot. In particular, the pre-formulation is easy to manufacture, may be sterile-filtered, has low viscosity (allowing easy and less painful administration typically through a narrow needle), allows a high level of bioactive agent to be incorporated (thus potentially allowing a smaller amount of composition to be used), requires shallower injection and/or forms a desired non-lamellar depot composition in vivo having a controllable "burst" or "non-burst" release profile. The compositions are also formed from materials that are non-toxic, biotolerable and biodegradable, which can be administered by i.m., or s.c. and are suitable for self-administration.

In a first aspect, the present invention thus provides a pre-formulation comprising a low viscosity mixture of:
a) at least one neutral diacyl lipid and/or a tocopherol;
b) at least one phospholipid;
c) at least one biocompatible, (preferably oxygen containing) organic solvent;
d) at least one GLP-1 analogue.
wherein the pre-formulation forms, or is capable of forming, at least one liquid crystalline phase structure upon contact with an aqueous fluid.

In one preferred embodiment, this pre-formulation will comprise a low-viscosity mixture of:
a) at least one diacyl glycerol;
b) at least one phosphatidyl choline;
c) at least one oxygen containing organic solvent;
d) at least one GLP-1 analogue;
wherein the pre-formulation forms, or is capable of forming, at least one liquid crystalline phase structure upon contact with an aqueous fluid.

Generally, the aqueous fluid will be a body fluid particularly extra-vascular fluid, extracellular fluid/interstitial fluid or plasma, and the pre-formulation will form a liquid crystalline phase structure when contacted with such a fluid (e.g. in vivo). The pre-formulation of the invention will generally not contain any significant quantity of water prior to administration.

In a second aspect of the invention, there is also provided a method of delivery of a GLP-1 analogue to a human or non-human animal (preferably mammalian) body, this method comprising parenterally administering (e.g. i.m. or preferably s.c.) a pre-formulation comprising a low viscosity mixture of:
a) at least one neutral diacyl lipid and/or a tocopherol;
b) at least one phospholipid;
c) at least one biocompatible, (preferably oxygen containing) organic solvent;
d) at least one GLP-1 analogue;
whereby to form at least one liquid crystalline phase structure upon contact with an aqueous fluid in vivo following administration. Preferably, the pre-formulation administered in such a method is a pre-formulation of the invention as described herein.

In a further aspect, the present invention also provides a method for the preparation of a liquid crystalline depot composition comprising exposing a pre-formulation comprising a low viscosity mixture of:
a) at least one neutral diacyl lipid and/or a tocopherol;
b) at least one phospholipid;
c) at least one biocompatible, (preferably oxygen containing) organic solvent;
d) at least one GLP-1 analogue;
to an aqueous fluid in vivo.

Preferably the pre-formulation administered is a pre-formulation of the present invention as described herein.

In a still further aspect the present invention provides a process for the formation of a pre-formulation suitable for the administration of a bioactive agent to a (preferably mammalian) subject, said process comprising forming a low viscosity mixture of
a) at least one neutral diacyl lipid and/or a tocopherol;
b) at least one phospholipid;
c) at least one biocompatible, (preferably oxygen containing) organic solvent;
and dissolving or dispersing at least one GLP-1 analogue in the low viscosity mixture, or in at least one of components a, b or c prior to forming the low viscosity mixture. Preferably the pre-formulation so-formed is a formulation of the invention as described herein.

In a yet still further aspect the present invention provides the use of a low viscosity mixture of:
a) at least one neutral diacyl lipid and/or a tocopherol;
b) at least one phospholipid;
c) at least one biocompatible, (preferably oxygen containing) organic solvent;
d) at least one GLP-1 analogue;
in the manufacture of a pre-formulation for use in the sustained administration of said GLP-1 analogue, wherein said pre-formulation is capable of forming at least one liquid crystalline phase structure upon contact with an aqueous fluid.

The invention also provides the use of a GLP-1 analogue composition as described herein in the manufacture of a medicament for the treatment of diabetes, especially type II diabetes, or for the medical or cosmetic treatment of excess bodyweight and/or obesity. In the case of medical treatment, the composition is typically administered to a subject in medical need thereof (e.g. having diabetes, excess bodyweight or obesity). In the case of cosmetic treatment, the subject may not have an identifiable medical need thereof, but may, for example, have a body mass index in the slightly overweight or higher normal, or normal range, wherein the benefit from weight loss is largely or solely cosmetic rather than medical.

In a still further aspect, the present invention provides a method for the treatment of a human or non-human mammalian subject in need thereof with a GLP-1 analogue, said method comprising administering to said subject a pre-formulation comprising a low-viscosity mixture of;
a) at least one neutral diacyl lipid and/or a tocopherol;
b) at least one phospholipid;
c) at least one biocompatible, (preferably oxygen containing) organic solvent;
d) at least one GLP-1 analogue;
Preferably, the method of treatment is a method for the treatment of at least one condition selected from diabetes, type-I diabetes, type II diabetes, excess bodyweight and obesity.

The invention further provides a method of treatment comprising administration of a GLP-1 analogue composition as described herein, especially in a subject in need thereof. The method of treatment is particularly for the treatment of diabetes, especially type II diabetes.

In a yet further aspect, the present invention provides the use of;
a) at least one neutral diacyl lipid and/or a tocopherol;
b) at least one phospholipid;
c) at least one biocompatible, (preferably oxygen containing) organic solvent;
d) at least one GLP-1 analogue;
in the manufacture of a low viscosity pre-formulation medicament for use in the in vivo formation of a depot for treatment of type-I diabetes, type II diabetes, excess bodyweight and/or obesity.

In all aspects of the present invention, components a)-c) will preferably be:
a) at least one diacyl glycerol and/or at least one tocopherol;
b) at least one phosphatidyl choline;
c) at least one oxygen containing organic solvent;

The pre-formulations of the present invention are highly advantageous in that they are stable to prolonged storage in their final "administration ready" form. As a result, they may readily be supplied for administration either by health professionals or by patients or their careers, who need not be fully trained health professionals and may not have the experience or skills to make up complex preparations. This is particularly important in long-duration, slow-effecting diseases such as diabetes.

In a yet further aspect, the present invention provides a disposable administration device (which is also to include a device component) pre-loaded with a measured dose of a pre-formulation of the present invention. Such a device will typically contain a single dose ready for administration, and will generally be sterile-packed such that the composition is stored within the device until administration. Suitable devices include cartridges, ampoules and particularly syringes and syringe barrels, either with integral needles or with standard (e.g. luer) fittings adapted to take a suitable disposable needle.

The pre-filled devices of the invention may also suitably be included in an administration kit, which kit also forms a further aspect of the invention. In a still further aspect, the invention thus provides a kit for the administration of at least one GLP-1 analogue, said kit containing a measured dose of a formulation of the invention and optionally an administration device or component thereof. Preferably the dose will be held within the device or component, which will be suitable for i.m. or preferably s.c. administration. The kits may include additional administration components such as needles, swabs, etc. and will optionally and preferably contain instructions for administration. Such instructions will typically relate to administration by a route as described herein and/or for the treatment of a disease indicated herein above.

The invention provides for a pre-filled administration device as indicated herein and a kit as indicated herein comprising a GLP-1 analogue composition as described herein.

In an alternative aspect of the present invention, the "kit" may contain at least two vessels, a first containing a low viscosity mixture of components a) to c), as described here, and a second containing a measured dose of at least one GLP-1 analogue as described herein. Such a "two component kit" may comprise GLP-1 powder in one vial or prefilled syringe and the lipid formulation of components a) to c) in a second vial or prefilled syringe. In the case of two syringes, before injection, the prefilled syringes are connected and the GLP-1 powder is mixed with the lipid formulation by moving the syringe barrels back and forth, forming a GLP-1 suspension which is injected. Alternatively, the liquid lipid formulation (a) to c)) is drawn from one vial, or is pre-filled into a syringe, and is injected into a vial containing GLP-1 powder. This formulation may subsequently be mixed by hand shaking or other suitable reconstitution method (e.g. vortex mixing etc.).

In this aspect, the invention therefore provides a two component kit comprising
i) a first vessel containing a low viscosity mixture of components a) to c) as described herein;
ii) a second vessel containing at least one GLP-1 analogue,
iii) optionally and preferably at least one of:
  1) at least one syringe (which may be one or both of said first and second vessels)
  2) a needle for administration, such as those described herein;
  3) instructions for generation of a composition of the invention from the contents of the first and second vessels;
  4) instructions for administration, whereby to form a depot as described herein.

The formulations of the present invention generate a non-lamellar liquid crystalline phase following administration. The use of non-lamellar phase structures (such as liquid crystalline phases) in the delivery of bioactive agents is now relatively well established. Such structures form when an amphiphilic compound is exposed to a solvent because the amphiphile has both polar and apolar groups which cluster to form polar and apolar regions. These regions can effectively solubilise both polar and apolar compounds. In addition, many of the structures formed by amphiphiles in polar and/or apolar solvents have a very considerable area of polar/apolar boundary at which other amphiphilic compounds can be adsorbed and stabilised. Amphiphiles can also be formulated to protect active agents, to at least some extent, from aggressive biological environments, including enzymes, and thereby provide advantageous control over active agent stability and release.

The formation of non-lamellar regions in the amphiphile/water, amphiphile/oil and amphiphile/oil/water phase diagrams is a well known phenomenon. Such phases include liquid crystalline phases such as the cubic P, cubic D, cubic G and hexagonal phases, which are fluid at the molecular level but show significant long-range order, and the L3 phase which comprises a multiply interconnected bi-continuous network of bilayer sheets which are non-lamellar but lack the long-range order of the liquid crystalline phases. Depending upon their curvature of the amphiphile sheets, these phases may be described as normal (mean curvature towards the apolar region) or reversed (mean curvature towards the polar region).

The non-lamellar liquid crystalline and L3 phases are thermodynamically stable systems. That is to say, they are not simply a meta-stable state that will separate and/or reform into layers, lamellar phases or the like, but are the stable thermodynamic form of the lipid/solvent mixture.

It is important that the pre-formulations of the invention are not liquid crystalline prior to administration because bulk liquid crystalline phase is generally highly viscous. The pre-formulations are thus low viscosity, non-liquid-crystalline formulations which undergo a phase change upon administration to form a liquid crystalline mass. Particularly preferred examples of low viscosity mixtures are molecular solutions and/or isotropic phases such as L2 and/or L3 phases. As described above, the L3 is a non-lamellar phase of interconnected sheets which has some phase structure but lacks the long-range order of a liquid crystalline phase. Unlike liquid crystalline phases, which are generally highly viscous, L3 phases are of lower viscosity. Obviously, mixtures of L3 phase and molecular solution and/or particles of L3 phase suspended in a bulk molecular solution of one or more components are also suitable. The L2 phase is the so-called "reversed micellar" phase or microemulsion. Most preferred low viscosity mixtures are molecular solutions, L3 phases and mixtures thereof. L2 phases are less preferred, except in the case of swollen $L_2$ phases as described below.

As used herein, the term "low viscosity mixture" is used to indicate a mixture which may be readily administered to a subject and in particular readily administered by means of a standard syringe and needle arrangement. This may be indicated, for example by the ability to be dispensed from a 1 ml disposable syringe through a small gauge needle. Preferably, the low viscosity mixtures can be dispensed through a needle of 19 awg, preferably smaller than 19 gauge, more preferably 23 awg (or most preferably even 27 gauge) needle by manual pressure. In a particularly preferred embodiment, the low viscosity mixture should be a mixture capable of passing through a standard sterile filtration membrane such as a 0.22 µm syringe filter. A typical range of suitable viscosities would be, for example, 0.1 to 5000 mPas, preferably 1 to 1000 mPas at 20° C.

It has been observed that by the addition of small amounts of low viscosity solvent, as indicated herein, a very significant change in viscosity can be provided. For example, the addition of only 5% solvent to a lipid mixture can reduce viscosity 100-fold and addition of 10% may reduce the viscosity up to 10,000 fold. In order to achieve this non-linear, synergistic effect, in lowering viscosity it is important that a solvent of appropriately low viscosity and suitable polarity be employed. Such solvents include those described herein infra.

The present invention provides a pre-formulation comprising components a, b, c and at least one GLP-1 analogue as indicated herein. The amounts of these components will typically be in the range 30-70% a), 30-60% b) and 0.1-20% c), with the GLP-1 analogue present at 0.01% to 10%, (such as 40-70% a), 30-60% b) and 0.1-10% c), with the GLP-1 analogue present at 0.1% to 10%). All % being by weight herein throughout, unless otherwise indicated. The formulations may consist of essentially only these components and in one aspect consist entirely of such components. Preferable ranges for component a) are 33-60% (e.g. 43-60%), particularly 35-55% (e.g. 45-55%) and preferable ranges of component b) are 33-55% (e.g. 35-55%), particularly 35-50% (e.g. 40 to 50%).

Ratios of a:b are typically 40:60 to 70:30, preferably 45:55 to 60:40 and more preferably 48:52 to 55:45. Ratios of around 50:50 are highly effective.

The amount of solvent component c) in the preformulation will have a considerable effect upon several features. In particular, the viscosity and the rate (and duration) of release will alter significantly with the solvent level. The amount of solvent will thus be at least sufficient to provide a low viscosity mixture but will additionally be determined so as to provide the desired release rate. This may be determined by routine methods in view of the Examples below. Typically a level of 0.1 to 20%, particularly 0.1 to 10% solvent will provide suitable release and viscosity properties. This will preferably be 2 to 15% (e.g. 2 to 8%) and an amount of around 5% is highly effective.

It is the remarkable finding of the present inventors that the proportion of solvent in the formulation can be used to "tune" the release profile of certain active agents during the first few days of release. In particular, with appropriate actives, although all formulations of the invention have a surprisingly low "burst/lag" effect (in fact there are may be no lag period at all), and reach a plateau release level within a few days (e.g. 5 days, preferably 3 days, more preferably 1 day) of injection, if a controlled "burst"/initial release of active agent is required in the first 1-2 days then this can be provided by increasing the solvent proportion to the upper region of the range given above. In contrast, in the mid- to lower-region of the range, a formulation giving a depot with essentially no burst and a rapid decline to the plateau release level is provided. The skilled worker will have no difficulty identifying those actives for which this "tuning" is suitable. in particular, actives which can be dissolved in the formulation to form a homogeneous solution are typically highly suitable, whereas those which are dispersed generally show a lesser effect.

Thus, in one embodiment, the present invention provides formulations and depots containing around 0.1 to 6 wt % component c) and having a low release of the active compound during the first days after administration ("non-burst profile"). In an alternative embodiment, the present invention provides formulations and depots containing around 6.5 to 10 wt % component c) and having higher initial release of the active compound during the first days after administration ("burst profile").

There is a certain embodiment of the present invention in which higher proportions of water may be tolerated. This is where water is present as a part of the solvent component in combination with an additional water-miscible component c (single solvent or mixture). In this embodiment, up to 20%, preferably up to 10 wt % water may be present providing that at least 3 wt %, preferably at least 5% and more preferably at least 7 wt % component c is also present, that component c is water miscible, and that the resulting preformulation remains non-viscous and thus does not form a liquid crystalline phase.

Generally the weight ratio between organic solvent component c) and water will be between 20:80 and 80:20, preferably 30:70 to 70:30 and more preferably 35:65 to 65:35. In one embodiment the proportion is at least 50% solvent. Most suitable solvents of use with water in this aspect of the invention include ethanol, isopropyl alcohol, NMP, acetone and ethyl acetate.

The low initial release ("non-burst profile") of active agent is defined such that the area under a plasma concentration against time the curve during the first 24 hours is less than 15% of the area under the curve for the entire curve (measured or extrapolated from time 0 to infinity or from time 0 to the last sampling time point), more preferably less than 10% and most preferable less than 7%. In addition, the decline to plateau plasma concentration levels after the initial peak should be rapid, such that plateau is reached within 48 hours, more preferably within 24 hours, and most preferably within 12 hours, Conversely, a high initial release ("burst profile") is such that more than 15% of active agent is released within 24 hours and more preferably more than 20% is released during the first 24 hours. The decline to plateau will not occur until after 36 hours, more preferably after 48 hours and most preferably after 72 hours. It is preferable that each of these profiles is combined with a rapid settling of the plasma active agent concentration to "plateau" level. For example, the plasma concentration after 10 days should be no more than 50% greater or less than the average concentration over days 5 to 20. Preferably this will be no more than 30% and more preferably no more than 20%.

As indicated above, the amount of component c in the pre-formulations of the invention will be at least sufficient to provide a low viscosity mixture (e.g. a molecular solution, see above) of components a, b and c and will be easily determined for any particular combination of components by standard methods. The phase behaviour itself may be analysed by techniques such as visual observation in combination with polarized light microscopy, nuclear magnetic resonance, and cryo-transmission electron microscopy (cryo-TEM) to look for solutions, L2 or L3 phases, or liquid crystalline phases or as in the case of cryoTEM, dispersed fragments of such phases. Viscosity may be measured directly by standard means. As described above, an appropriate practical viscosity is that which can effectively be syringed and particularly sterile filtered. This will be assessed easily as indicated herein.

Component "a" as indicated herein is at least one diacyl glycerol (DAG) and thus has two non-polar "tail" groups. The two non-polar groups may have the same or a differing number of carbon atoms and may each independently be saturated or unsaturated. Examples of non-polar groups include $C_6$-$C_{32}$ alkyl and alkenyl groups, which are typically present as the esters of long chain carboxylic acids. These are often described by reference to the number of carbon atoms and the number of unsaturations in the carbon chain. Thus, CX:Z indicates a hydrocarbon chain having X carbon atoms and Z unsaturations. Examples particularly include caproyl (C6:0), capryloyl (C8:0), capryl (C10:0), lauroyl (C12:0), myristoyl (C14:0), palmitoyl (C16:0), phytanoyl (C16:0), palmitoleyl (C16:1), stearoyl (C18:0), oleoyl (C18:1), elaidoyl (C18:1), linoleyl (C18:2), linolenoyl (C18:3), arachidonoyl (C20:4), behenoyl (C22:0) and lignoceroyl (C24:9) groups. Thus, typical non-polar chains are based on the fatty acids of natural ester lipids, including caproic, caprylic, capric, lauric, myristic, palmitic, phytanic, palmitolic, stearic, oleic, elaidic, linoleic, linolenic, arachidonic, behenic or lignoceric acids, or the corresponding alcohols. Preferable non-polar chains are palmitic, stearic, oleic and linoleic acids, particularly oleic acid.

Mixtures of any number of diacyl lipids may be used as component a. Preferably this component will include at least a portion of glycerol dioleate (GDO). A highly preferred example is DAG comprising at least 50%, preferably at least 80% and even comprising substantially 100% GDO.

Since GDO and other diacyl glycerols are products derived from natural sources, there is generally a certain proportion of "contaminant" lipid having other chain lengths etc. In one aspect, GDO as used herein is thus used to indicate any commercial grade of GDO with concomitant impurities (i.e. GDO of commercial purity). These impurities may be separated and removed by purification but providing the grade is consistent this is rarely necessary. If necessary, however, "GDO" may be essentially chemically pure GDO, such as at least 80% pure, preferably at least 85% pure and more preferably at least 90% pure GDO.

Component "b" in the present invention is at least one phosphatidyl choline (PC). As with component a, this component comprises a polar head group and at least one non-polar tail group. The difference between components a and b lies principally in the polar group. The non-polar portions may thus suitably be derived from the fatty acids or corresponding alcohols considered above for component a. As with component a), the PC will contain two non-polar groups.

The phosphatidyl choline portion, even more suitably than any diacyl glycerol portion, may be derived from a natural source. Suitable sources of phospholipids include egg, heart (e.g. bovine), brain, liver (e.g. bovine) and plant sources including soybean. Such sources may provide one or more constituents of component b, which may comprise any mixture of phospholipids. Any single PC or mixture of PCs from these or other sources may be used, but mixtures comprising soy PC or egg PC are highly suitable. The PC component preferably contains at least 50% soy PC or egg PC, more preferably at least 75% soy PC or egg PC and most preferably essentially pure soy PC or egg PC.

Since the pre-formulations of the invention are to be administered to a subject for the controlled release of a GLP-1 analogue active agent, it is important that the components are biocompatible. In this regard, the pre-formulations of the present invention are highly advantageous since both PC and DAGs are well tolerated and are broken down in vivo into components that are naturally present in the mammalian body.

A particularly favoured combination of components a and b are GDO with PC, especially GDO with soy PC.

Component "c" of the pre-formulations of the invention is an oxygen containing organic solvent. Since the pre-formulation is to generate a depot composition following administration (e.g. in vivo), upon contact with an aqueous fluid, it is desirable that this solvent be tolerable to the subject and be capable of mixing with the aqueous fluid, and/or diffusing or dissolving out of the pre-formulation into the aqueous fluid. Solvents having at least moderate water solubility are thus preferred.

In a preferred version, the solvent is such that a relatively small addition to the composition comprising a and b, i.e. preferably below 10%, give a large viscosity reductions of one order of magnitude or more. As described herein, the addition of 10% solvent can give a reduction of two, three or even four orders of magnitude in viscosity over the solvent-free composition, even if that composition is a solution or $L_2$ phase containing no solvent, or an unsuitable solvent such as water, or glycerol.

Typical solvents suitable for use as component c include at least one solvent selected from alcohols, ketones, esters (including lactones), ethers, amides and sulphoxides. Alcohols are particularly suitable and form the preferred class of solvents. Examples of suitable alcohols include ethanol, isopropanol, benzyl alcohol and glycerol formal. Ethanol is most preferred. Monools are preferred to diols and polyols. Where diols or polyols are used, this is preferably in combination with an at least equal amount of monool or other preferred solvent. Examples of ketones include acetone, and propylene carbonate. Suitable ethers include diethylether, glycofurol, diethylene glycol monoethyl ether, dimethylisobarbide, and polyethylene glycols. Suitable esters include ethyl acetate, benzyl benzoate and isopropyl acetate and dimethyl sulphide is as suitable sulphide solvent. Suitable amides include n-methylpyrrolidone (NMP), 2-pyrrolidone and dimethylacetamide (DMA). Sulphoxides include methylsulphoxide and dimethylsulphoxide (DMSO).

A highly preferred combination is soy PC, GDO and ethanol.

It is preferable that little or none of component c contains halogen substituted hydrocarbons since these tend to have lower biocompatibility. Where a portion of halogenated solvent such as dichloromethane or chloroform is necessary, this proportion will generally be minimised.

Component c as used herein may be a single solvent or a mixture of suitable solvents but will generally be of low viscosity. This is important because one of the key aspects of the present invention is that it provides pre-formulations that are of low viscosity and a primary role of a suitable solvent is to reduce this viscosity. This reduction will be a combination of the effect of the lower viscosity of the solvent and the effect of the molecular interactions between solvent and lipid composition. One observation of the present inventors is that the oxygen-containing solvents of low viscosity described herein have highly advantageous and unexpected molecular interactions with the lipid parts of the composition, thereby providing a non-linear reduction in viscosity with the addition of a small volume of solvent.

The viscosity of the "low viscosity" solvent component c (single solvent or mixture) should typically be no more than 18 mPas at 20° C. This is preferably no more than 15 mPas, more preferably no more than 10 mPas and most preferably no more than 7 mPas at 20° C.

A further advantage of the present pre-formulations is that a higher level of bioactive agent may be incorporated into the system. In particular, by appropriate choice of components a-c (especially c), high levels of active agent may be dissolved or suspended in the pre-formulations. This allows a reduction in the administered volume and thus less discomfort to subjects.

The pre-formulations of the present invention typically do not contain significant amounts of water. Since it is essentially impossible to remove every trace of water from a lipid composition, this is to be taken as indicating that only such minimal trace of water exists as cannot readily be removed. Such an amount will generally be less than 1% by weight, preferably less that 0.5% by the weight of the pre-formulation. In one preferred aspect, the pre-formulations of the invention do not contain glycerol, ethylene glycol or propylene glycol and contain no more than a trace of water, as just described.

The pre-formulations of the present invention contain one or more GLP-1 analogues or other active (see below) (which are intended by any reference to "active agents" herein). Since GLP-1 is a peptide hormone, typical GLP-1 analogues will be peptides, especially of around 30 amino acids, e.g. 20 to 45, especially 25 to 38. Preferably such peptides will be structurally related to GLP-1 and/or one or more of the known analogues, including those listed here. Peptides may contain only amino acids selected from those 20 α-amino acids indicated in the genetic code, or more preferably may contain their isomers and other natural and non-natural amino acids, (generally α, β or γ amino acids) and their analogues and derivatives. Preferred amino acids include those listed above as constituents of the known GLP-1 analogues.

Amino acid derivatives are especially useful at the termini of the peptides, where the terminal amino or carboxylate group may be substituted by or with any other functional group such as hydroxy, alkoxy, carboxy, ester, amide, thio, amido, amino, alkyl amino, di- or tri-alkyl amino, alkyl (by which is meant, herein throughout $C_1$-$C_{12}$ alkyl, preferably $C_1$-$C_6$ alkyl e.g. methyl, ethyl, n-propyl, isopropyl, n-butyl, iso-, sec- or t-butyl etc.), aryl (e.g phenyl, benzyl, napthyl etc) or other functional groups, preferably with at least one heteroatom and preferably having no more than 10 atoms in total, more preferably no more than 6.

By "GLP-1 analogue", as used herein is indicated any GLP-1 receptor agonist (or less preferably antagonist), including naturally occurring forms of GLP-1, either human or from any other species. These analogues are preferably peptides, peptide derivatives or peptide mimics. Peptide derived GLP-1 agonists are most preferred, such as those indicated above and especially GLP-1(7-37), GLP-1(7-36) amide, Liraglutide, AVE-010 (ZP10), TH0318 and Exenatide.

In one typical embodiment, the GLP-1 analogue will generally be formulated as 0.02 to 12% by weight of the total formulation. Typical values will be 0.1 to 10%, preferably 0.2 to 8% and more preferably 0.5 to 6%. A GLP-1 analogue content of around 1-5% is most preferable.

In a related embodiment, the GLP-1 analogue will generally be formulated as 0.01 to 12% by weight of the total formulation. Typical values will be 0.05 to 10%, preferably 0.1 to 8% and more preferably 0.2 to 6%. A GLP-1 analogue content of around 0.3-5% is most preferable.

Doses of the GLP-1 analogue suitable for inclusion in the formulation, and thus the volume of formulation used will depend upon the release rate (as controlled, for example by the solvent type and amount used) and release duration, as well as the desired therapeutic level, the activity of the specific agent, and the rate of clearance of the particular active chosen. Typically an amount of around 0.05 to 10 mg per week of depot duration, preferably 0.1 to 8 mg per week duration for a duration of 1 to 24 weeks, preferably 2 to 16 (e.g. 12) weeks. A total dose of 0.05 to 250 mg per dose would be suitable for providing a therapeutic level for between 7 and 168 days. This will preferably be 0.1 to 192 mg, e.g. 0.2 to 160 mg, 0.1 to 1.6 mg, 20 to 160 mg etc. Evidently, the stability of the active and linearity of the release rate will mean that the loading to duration may not be a linear relationship. A depot administered every 30 days might have, for example 0.2 to 20 mg or a 90 day depot have 60 to 120 mg of active, such as one of the GLP-1 analogues indicated herein. Evidently also, the biological half-life of the specific active will be particularly important. The half-life of native human GLP-1 (GLP-1(7-37) and GLP-1(7-36)amide), which is one preferred active, is less than 5 minutes, and so for sustained release, a relatively large amount (e.g. towards the higher end of the range) will be needed. For an analogue such as exenatide, with a much longer half-life, the amount needed will evidently be lower.

It is a remarkable development of the present formulations that native human GLP-1 (GLP-1(7-37) and GLP-1(7-36) amide) can be prepared and administered in a depot precursor of the present invention, and will provide controlled release over several days or even weeks, in spite of the remarkably short biological half-life of the active agent. Such a high performance in delivery of a short half-life active is not otherwise known and no other lipid depot system capable of sustained release of native human GLP-1 has been reported. Thus, in one embodiment, the active agent has a half-life of less than 1 hour, e.g. less than 15 minutes (such as GLP-1 (7-37)) and the preformulation forms a depot which provides sustained release for at least 7 days, preferably at least 14 days, more preferably at least 28 days.

In one particularly preferred embodiment of the present invention, the compositions (preformulations and resulting depots) may include at least one biocompatible polyethyleneoxide or poly(ethylene glycol) (PEG) fragmentation agent, such as a PEG grafted lipid and/or surfactant. These agents are useful in all compositions, and are believed to increase the stability of the GLP-1 analogue, even at low concentrations. In a particularly advantageous embodiment, however, they may be highly useful for providing depots with shorter duration (e.g. 5 to 30 days, especially 7 to 21 days). This is because such a component will tend to fragment the depot into smaller pieces in situ and thus the degradation of the depot will not only be biodegradation but also "physical" erosion, thus enabling faster release (but still without any significant burst release).

If included in the formulation, the content of such a fragmentation agent component, would be 0.1-20%, more preferably 0.5-18% and most preferably 1-15%. In particular, 0.1 to 1% (preferably 0.2 to 0.7%) is particularly useful for stabilising the GLP-1 analogue, and 1 to 15%, preferably 5 to 10% is beneficial in controlling the depot release period. Another advantage of including a fragmentation agent is that it may be beneficial from a chronic use point of view. Users of GLP-1 analogue depot products are typically likely to be long-terms users, and such a depot erodes faster and thus the depot will vanish faster from the injection site, allowing earlier re-use of the site and causing a lesser build-up of connective tissue around the sites of injection. Furthermore, the inclusion of such an agent may even improve the already good biotolerability/biocompatibility.

The most preferred fragmentation agent is Polysorbate 80 (P80). Other useful agents include other Polysorbates (e.g. Polysorbate 20), PEGylated phospholipids (PEG-lipids such as DSPE-PEG(2000), DSPE-PEG(5000), DOPE-PEG(2000) and DOPE-PEG(5000)), Solutol HS 15, PEGylated fatty acids (e.g. PEG-oleate), block co-polymers such as Pluronic® F127 and Pluronic® F68, ethoxylated castor oil derivatives (e.g. Chremophores), PEGylated glyceryl fatty acid esters (such as TMGO-15 from Nikko Chemicals) and PEGylated tocopherols (such as d-alpha tocopheryl poly(ethylene glycol)1000 succinate known as Vitamin E TPGS from Eastman).

The GLP-1 as a powder (e.g. in the kit of the invention), as well as GLP-1 dissolved in the lipid formulation, may gain stability (both storage and in vivo stability) by certain stabilising additives. Such additives include sugars (e.g. sucrose, trehalose, lactose etc.), polymers (e.g. polyols such as carboxy methyl cellulose), small amounts of surface active agents (e.g. P80—see above), antioxidants (such as ascorbic acid, EDTA and citric acid), amino acids (such as methionine, glutamate, lysine etc.) and anionic lipids and surface active agents (such as dioleoyl phosphatidyl glycerol (DOPG), palmitoyloleoyl phosphatidylglycerol (POPG) and oleic acid (OA)).

The pre-formulations of the present invention are formulated to be administered parenterally. This administration will generally not be an intra-vascular method but will preferably be subcutaneous, intracavitary or intramuscular. Typically the administration will be by injection, which term is used herein to indicate any method in which the formulation is passed through the skin, such as by needle, catheter or needle-less (needle-free) injector.

Preferred parenteral administration is by i.m or s.c. injection, most preferably by deep s.c. injection. An important feature of the composition of the invention is that it can be administered both by i.m. and s.c. and other routes without toxicity or significant local effects. It is also suitable for intracavital administration. The deep s.c. injection has the advantage of being less deep and less painful to the subject than the (deep) i.m. injection used for some current depots and is technically most suitable in the present case as it combines ease of injection with low risk of local side effects. It is a surprising observation of the present inventors that the formulations provide sustained release of active agent over a predictable time period by both subcutaneous and intramuscular injection. This therefore allows the site of injection to be varied widely and allows the dose to be administered without detailed consideration of the tissue depth at the site of injection.

The pre-formulations of the present invention provide non-lamellar liquid crystalline depot compositions upon exposure to aqueous fluids, especially in vivo. As used herein, the term "non-lamellar" is used to indicate a normal or reversed liquid crystalline phase (such as a cubic or hexagonal phase) or the L3 phase or any combination thereof. The term liquid crystalline indicates all hexagonal, all cubic liquid crystalline phases and/or all mixtures thereof. Hexagonal as used herein indicates "normal" or "reversed" hexagonal (preferably reversed) and "cubic" indicates any cubic liquid crystalline phase unless specified otherwise.

For many combinations of lipids, only certain non-lamellar phases exist, or exist in any stable state. It is a surprising feature of the present invention that compositions as described herein frequently exhibit non-lamellar phases which are not present with many other combinations of components. In one particularly advantageous embodiment, therefore, the present invention relates to compositions having a combination of components for which an $I_2$ and/or $L_2$ phase region exists when diluted with aqueous solvent. The presence or absence of such regions can be tested easily for any particular combination by simple dilution of the composition with aqueous solvent and study of the resulting phase structures by the methods described herein.

In a highly advantageous embodiment, the compositions of the invention may form an $I_2$ phase, or a mixed phase including $I_2$ phase upon contact with water. The $I_2$ phase is a reversed cubic liquid crystalline phase having discontinuous aqueous regions. This phase is of particular advantage in the controlled release of active agents and especially in combination with polar active agents, such as water soluble actives because the discontinuous polar domains prevent rapid diffusion of the actives. Depot precursors in the $L_2$ are highly effective in combination with an $I_2$ phase depot formation. This is because the $L_2$ phase is a so-called "reversed micellar" phase having a continuous hydrophobic region surrounding discrete polar cores. $L_2$ thus has similar advantages with hydrophilic actives. In transient stages after contact with body fluid the composition can comprise multiple phases since the formation of an initial surface phase will retard the passage of solvent into the core of the depot, especially with substantial sized administrations of internal depots. Without being bound by theory, it is believed that this transient formation of a surface phase, especially a liquid crystalline surface phase, serves to dramatically reduce the "burst/lag" profile of the present compositions by immediately restricting the rate of exchange between the composition and the surroundings. Transient phases may include (generally in order from the outside towards the centre of the depot): $H_{II}$, or $L_\alpha$, $I_2$, $L_2$, and liquid (solution). It is highly preferred that the composition of the invention is capable forming at least two and more preferably at least three of these phases simultaneously at transient stages after contact with water at physiological temperatures. In particular, it is highly preferred that one of the phases formed, at least transiently, is the $I_2$ phase. A further important combination is the phases $H_{II}$, $L_2$ and liquid (solution or dispersion), which is a highly favoured combination that will coexist after exposure (of certain favoured compositions of the invention) to body fluids ($H_{II}$ outermost to liquid innermost). The skilled reader will have no difficulty in identifying those compositions conforming to this requirement by reference to the description and Examples provided herein, but the most favoured compositional area for this behaviour is where ration of components a:b are in the region of equality (e.g. around 35:65 to 65:35, preferably 42:58 to 58:42, most preferably 46:54 to 54:46)

It is important to appreciate that the pre-formulations of the present invention are of low viscosity. As a result, these pre-formulations must not be in any bulk liquid crystalline phase since all liquid crystalline phases have a viscosity significantly higher than could be administered by syringe or spray dispenser. The pre-formulations of the present invention will thus be in a non-liquid crystalline state, such as a solution, $L_2$ or $L_3$ phase, particularly solution or $L_2$. The $L_2$ phase as used herein throughout is preferably a "swollen" $L_2$ phase containing greater than 10 wt % of solvent (component c) having a viscosity reducing effect. This is in contrast to a "concentrated" or "unswollen" $L_2$ phase containing no solvent, or a lesser amount of solvent, or containing a solvent (or mixture) which does not provide the decrease in viscosity associated with the oxygen-containing, low viscosity solvents specified herein.

Upon administration, the pre-formulations of the present invention undergo a phase structure transition from a low viscosity mixture to a high viscosity (generally tissue adherent) depot composition. Generally this will be a transition from a molecular mixture, swollen $L_2$ and/or L3 phase to one or more (high viscosity) liquid crystalline phases such as normal or reversed hexagonal or cubic liquid crystalline phases or mixtures thereof. As indicated above, further phase transitions may also take place following administration. Obviously, complete phase transition is not necessary for the functioning of the invention but at least a surface layer of the administered mixture will form a liquid crystalline structure. Generally this transition will be rapid for at least the surface region of the administered formulation (that part in direct contact with air, body surfaces and/or body fluids). This will most preferably be over a few seconds or minutes (e.g. up to 30 minutes, preferably up to 10 minutes, more preferably 5 minutes of less). The remainder of the composition may change phase to a liquid crystalline phase more slowly by diffusion and/or as the surface region disperses.

In one preferred embodiment, the present invention thus provides a pre-formulation as described herein of which at least a portion forms a hexagonal liquid crystalline phase upon contact with an aqueous fluid. The thus-formed hexagonal phase may gradually disperse and/or degrade, releasing the active agent, or may subsequently convert to a cubic liquid crystalline phase, which in turn then gradually disperses.

Without being bound by theory, it is believed that upon exposure (e.g. to body fluids), the pre-formulations of the invention lose some or all of the organic solvent included therein (e.g. by diffusion) and take in aqueous fluid from the bodily environment (e.g. the in vivo environment) such that at least a part of the formulation generates a non-lamellar, particularly liquid crystalline phase structure. In most cases these non-lamellar structures are highly viscous and are not easily dissolved or dispersed into the in vivo environment. The result is a monolithic "depot" generated in vivo with only a limited area of exposure to body fluids. Furthermore, because the non-lamellar structure has large polar, apolar and boundary regions, it is highly effective in solubilising and stabilising active agents such as peptides and protecting these from degradation mechanisms. As the depot composition formed from the pre-formulation gradually degrades over a period of days, weeks or months, the active agent is gradually released and/or diffuses out from the composition. Since the environment within the depot composition is relatively protected, the pre-formulations of the invention are highly suitable for active agents with a relatively low biological half-life (see above).

The depot systems formed by the formulations of the present invention are highly effective in protecting the active agent from degradation and thus allow an extended release period. Comparative tests have been carried out between the known PLGA slow-release product and formulations of the present invention containing GDO, soy PC, ethanol and active agents. These indicate that formulations of the present invention give lesser degradation under simulated in vivo conditions than known compositions. The formulations of the invention thus may provide in vivo depots of GLP-1 analogues which require administration only once every 7 to 360 days (e.g. 20 to 360 days), preferably 30 to 240 days (e.g. 30 to 168 days), more preferably 60 to 180 days (e.g. around 90 days). Alternatively, in a further preferred embodiment, the durations are somewhat shorter, preferably 10 to 240 days (e.g. 20 to 168 days), more preferably 14 to 180 days (e.g. around 60 days). Evidently, a longer stable release period is desirable for patient comfort and compliance, as well as demanding less time from health professionals if the composition is not to be self-administered. Where the composition is to be self-administered, patient compliance may be aided by a weekly (e.g. every 7 days) or monthly (e.g. every 28 or 30 days) administration so that the need to administer is not forgotten.

A considerable advantage of the depot precursors of the present invention is that they are stable homogeneous phases. That is to say, they may be stored for considerable periods (preferably at least 6 months) at room or refrigerator temperature, without phase separation. As well as providing advantageous storage and facile administration, this allows for the dose of GLP-1 analogue to be selected by reference to the species, age, sex, weight, and/or physical condition of the individual subject, by means of injecting a selected volume. Furthermore, the present inventors have surprisingly found that the initial release of active agent (observed as $C_{max}$) is not proportional to dose volume, in ranges of at least 10-fold in sample volume injection, while the total drug exposure (observed as AUC or mean plateau plasma concentration) is proportional to the injection volume. On the contrary, it has been shown that $C_{max}$ can be correlated to the surface area of the injected dose volume. That is, $C_{max}$ is proportional to the two-third power of the injected dose volume. Increasing the dose volume by a factor of 10 will not increase the $C_{max}$ 10 times and the relationship between $C_{max}$ and the total drug exposure (AUC or mean plateau plasma concentration level) will thus decrease with increasing dose volume. This is highly advantageous, because this property reduce the risk of reaching potentially toxic plasma drug concentrations even if the total dose is significantly increased. As considered above, this may be a key concern in going from a twice-daily administration to a sustained formulation without provoking hypoglycaemia. Even in situations where dosing is not directly proportional to injection volume, however, the homogenous nature of the depot precursors importantly allow for partial administration of a pre-measured dose and this administration may be made by reference to a dosing table, chart, software calculation etc. which may take into account any or all relevant subject variables.

The present invention thus provides for methods comprising the selection of a dosing amount specific to an individual, particularly by subject weight. The means for this dose selection being by administration volume.

It is an unexpected finding of the present inventors that the pre-formulations result in a depot composition that have very little "burst" effect in the active agent release profile. This is unexpected because it might be expected that the low viscosity mixture (especially if this is a solution) of the pre-composition would rapidly lose active agent upon exposure to water in the way that is observed for certain other sustained release formulations. In fact, pre-formulations of the invention have shown considerably less of an initial "burst" than previously known polymer-based depot compositions, including microbead compositions, which tend to have an initial "wash off" or "wash out" of surface-bound or dissolved active agent. In one embodiment, the invention thus provides injectable pre-formulations and resulting depot compositions wherein the highest plasma concentration of active after administration is no more than 40 times the average concentration between 24 hours and 5 days of administration. This ratio is preferably no more than 25 times and most preferably no more than 20 times (e.g. up to 10 or up to 5 times) the average concentration.

The compositions of the invention also allow for the generation of depot compositions with very little "lag" effect after administration. In a further embodiment, the invention thus provides injectable pre-formulations and resulting depot compositions wherein the plasma concentration of active at 7 days after a single administration is no lower than the plasma concentration of active at 21 days after administration. Similarly, the concentration of active should be higher at all times in the first 21 days than the concentration at any time from 30 days after administration onwards. This gradually decaying release profile has not previously been demonstrated for lipid depot slow release GLP-1 analogue formulation.

In combination with the features and preferred features indicated herein, the pre-formulations of the invention may have one or more of the following preferred features independently or in combination:

Component a) comprises, consists essentially of or preferably consists of GDO;

Component b) comprises, consists essentially of or preferably consists of soy PC;

Component c) comprises, consists essentially of or preferably consists of a 1, 2, 3 or 4 carbon alcohol, preferably isopropanol or more preferably ethanol;

The pre-formulation contains at least one GLP-1 analogue selected from those indicated herein, preferably GLP-1(7-37), GLP-1(7-36)amide, Liraglutide, AVE-010, TH-0318 or exenatide;

The pre-formulation has a low viscosity as indicated herein.

The pre-formulation forms a liquid crystalline phase as indicated herein upon in vivo administration.

The pre-formulation generates a depot following in vivo administration, which depot releases at least one GLP-1 analogue at a therapeutic level over a period of at least 7 days, preferably at least 21 days, more preferably at least 30 days.

In combination with the features and preferred features indicated herein, the method(s) of treatment of the present invention may have one or more of the following preferred features independently or in combination:

The method comprises the administration of at least one formulation with one or more preferred features as indicated above;
The method comprises the administration of at least one formulation as indicated herein by i.m., s.c. or preferably deep s.c. injection;
The method comprises administration by means of a pre-filled administration device as indicated herein;
The method comprises administration through a needle no larger than 20 gauge, preferably smaller than 20 gauge, and most preferably 23 gauge or smaller;
The method comprises a single administration every 7 to 360 days, preferably 7 to 120 days, more preferably 14 to 60 days.
The method comprises a single administration every 14 to 180 days, preferably around 60 days.

In combination with the features and preferred features indicated herein, the use(s) of the pre-formulations indicated herein in the manufacture of medicaments may have one or more of the following preferred features independently or in combination:

The use comprises the use of at least one formulation with one or more preferred features as indicated above;
The use comprises the manufacture of a medicament for administration of at least one formulation as indicated herein by i.m., s.c. or preferably deep s.c. injection;
The use comprises the manufacture of a medicament for administration by means of a pre-filled administration device as indicated herein;
The use comprises the manufacture of a medicament for administration through a needle no larger than 20 gauge, preferably smaller than 20 gauge, and most preferably 23 gauge or smaller;
The use comprises the manufacture of a medicament for administration once every 7 to 360 days, preferably 7 to 120 days, more preferably 14 to 60 days.

In combination with the features and preferred features indicated herein, the pre filled devices of the invention may have one or more of the following preferred features independently or in combination:

They contain a preferred formulation as indicated herein;
They comprise a needle smaller than 20 gauge, preferably no larger than 23 gauge;
They contain a single dose of 0.05 to 250 mg of GLP-1 analogue, preferably 0.1 to 100 mg and more preferably 1-50 mg;
They contain GLP-1(7-37), GLP-1(7-36)amide, TH-0318, Liraglutide or AVE-010, at around 0.05 to 250 mg;
They contain a homogeneous mixture of a composition of the invention in ready-to-inject form.
They contain a formulation of components a) to c) for combination with a GLP-1 analogue whereby to form a preformulation of the invention.
They contain a GLP-1 analogue for combination with a formulation of components a) to c), whereby to form a pre-formulation of the invention.
They contain a total volume for administration of no more than 5 ml, preferably no more than 3 ml more preferably no more than 2 ml.

In combination with the features and preferred features indicated herein, the kits of the invention may have one or more of the following preferred features independently or in combination:

They contain a preferred formulation as indicated herein;
They contain a pre-filled device as indicated herein;
They contain a needle smaller than 20 gauge, preferably no larger than 23 gauge;
They contain a single dose of 0.05 to 250 mg of GLP-1 analogue, preferably 0.1 to 100 mg and more preferably 1-50 mg;
They contain GLP-1(7-37), GLP-1(7-36)amide, TH-0318, Liraglutide or AVE-010, at around 0.05 to 250 mg;
They contain a "two compartment kit" comprising at least two vessels containing a lipid formulation of the invention and a GLP-1 analogue powder, respectively.
They contain a total volume for administration of no more than 5 ml, preferably no more than 3 ml more preferably no more than 2 ml.
They contain instructions for administration by a route and/or at a frequency as indicated herein;
They contain instructions for administration for use in a method of treatment as described herein.

The Invention will now be further illustrated by reference to the following non-limiting Examples and the attached Figures, in which;

FIG. 1 shows the plasma profile of GLP-1(7-36)amide after subcutaneous administration of two formulations comprising GLP-1(7-36)amide and one placebo formulation to male Sprague-Dawley rats (n=6).

EXAMPLES

Abbreviations Used:

GLP-1 = GLP-1(7-36)amide (acetate salt) = Glucagon-like peptide 1 (PolyPeptide Laboratories, Germany)
SPC = Soy Phosphatidyl Choline (Lipoid, Germany)
EPC = Egg Phosphatidyl Choline (Lipoid, Germany)
GDO = Glycerol Dioleate (Danisco, Denmark)
P80 = Polysorbate 80 (Apoteket, Sweden)
F68 = Pluronic F68 (Sigma-Aldrich, Sweden)
EtOH = Ethanol (Kemetyl, Sweden)
HAc = Acetic acid (Merck, Germany)
BzOH = Benzyl alcohol (Apoteket, Sweden)
PG = Propylene glycol (Apoteket, Sweden)
BzB = Benzyl benzoate (Apoteket, Sweden)
NMP = N-methyl pyrrolidone (ISP, USA)
Ascorbic acid = Asc (Sigma-Aldrich, Sweden)
EDTA = Ethylenediamine tetraacetic acid (Sigma-Aldrich, Sweden)
DPP-IV = Dipeptidyl Peptidase IV
DOPG = Dioleoyl Phosphatidyl Glycerol (Avanti Polar Lipids, U.S.A.)

Example 1

Availability of Various Liquid Crystalline Phases in the Depot by Choice of Composition Injectable formulations containing different proportions of phosphatidyl choline ("PC"—Lipoid S100) and glycerol dioleate (GDO) and with EtOH as solvent were prepared to illustrate that various liquid crystalline phases can be accessed after equilibrating the depot precursor formulation with excess water.

Appropriate amounts of PC, GDO and EtOH were weighed in glass vials and the mixture was placed on a shaker until the PC completely dissolved to form a clear liquid solution. GDO was then added to form an injectable homogenous solution.

Each formulation was injected in a vial and equilibrated with excess water. The phase behaviour was evaluated visually and between crossed polarizes at 25° C. Results are presented in Table 1.

TABLE 1

| Formulation | PC (wt %) | GDO (wt %) | EtOH (wt %) | Phase in $H_2O$ |
|---|---|---|---|---|
| A | 22.5 | 67.5 | 10.0 | $L_2$ |
| B | 28.8 | 61.2 | 10.0 | $I_2$ |
| C | 45.0 | 45.0 | 10.0 | $I_2/H_{II}$ |
| D | 63.0 | 27.0 | 10.0 | $H_{II}/L_\alpha$ |

$L_2$ = reversed micellar phase
$I_2$ = reversed cubic liquid crystalline phase
$H_{II}$ = reversed hexagonal liquid crystalline phase
$L_\alpha$ = lamellar phase Example 2

Viscosity in PC/GDO Mixtures on Addition of Co-solvent

Mixtures of PC/GDO and co-solvent were prepared according to the methods of Example 1. The EtOH content was adjusted by first evaporating the EtOH from the PC/GDO-mixture on a rotary evaporator leaving a viscous liquid mixture of essentially only PC and GDO. Co-solvents were then added in the proportions indicated in Table 2 below.

The samples were allowed to equilibrate for several days before viscosity measurements were performed using a Physica UDS 200 rheometer at 25° C.

TABLE 2

| Sample | PC/GDO (wt/wt) | EtOH/ wt % | Glycerol/ wt % | $H_2O$/ wt % | Viscosity/ mPas |
|---|---|---|---|---|---|
| 1 | 50/50 | 3 | — | — | 1900 |
| 2 | 50/50 | 5 | — | — | 780 |
| 3 | 50/50 | 7 | — | — | 430 |
| 4 | 50/50 | 8 | — | — | 300 |
| 5 | 50/50 | 10 | — | — | 210 |
| 6 | 50/50 | 15 | — | — | 100 |
| 7 | 45/55 | 3 | — | — | 1350 |
| 8 | 45/55 | 5 | — | — | 540 |
| 9 | 45/55 | 7 | — | — | 320 |
| 10 | 45/55 | 8 | — | — | 250 |
| 11 | 45/55 | 10 | — | — | 150 |
| 12 | 45/55 | 15 | — | — | 85 |
| 13 | 40/60 | 3 | — | — | 740 |
| 14 | 40/60 | 5 | — | — | 400 |
| 15 | 40/60 | 7 | — | — | 240 |
| 16 | 40/60 | 8 | — | — | 200 |
| 17 | 40/60 | 10 | — | — | 130 |
| 18 | 40/60 | 15 | — | — | 57 |
| 19 | 40/60 | — | 10 | — | $8*10^6$ |
| 20 | 40/60 | — | — | 3 | $2.5*10^8$ |
| 21 | 40/60 | — | — | 5 | $4*10^7$ |

This example illustrates the need for a solvent with viscosity lowering properties in order to obtain injectable formulations. The mixtures containing glycerol (sample 19) or water (samples 20 and 21) are too viscous to be injectable at solvent concentrations equivalent to the samples containing EtOH (compare with samples 13, 14 and 17).

Example 3

Degradation of Depot Formulation in the Rat

Various volumes (1, 2, 6 ml/kg) of the depot precursor (36% wt PC, 54% wt GDO, and 10% wt EtOH) were injected in the rat and were removed again after a period of 14 days. It was found that substantial amounts of the formulations were still present subcutaneously in the rat after this time, see Table 3.

TABLE 3

| Dose (ml/kg) | Mean diameter day 3 (mm) | Mean diameter day 14 (mm) |
|---|---|---|
| 1 (n = 3) | 15.8 | 12.5 |
| 2 (n = 3) | 18.5 | 15.3 |
| 6 (n = 3) | 23.3 | 19.3 |

Example 4

Preparation of Depot Compositions of Glucagon-like Peptide 1 (GLP-1)

Depot precursors of GLP-1 were prepared in two different ways:

1) GLP-1 was first mixed with PC, GDO and EtOH where EtOH was added in excess to facilitate mixing. Typically, the EtOH content at this stage was about 50-80 wt %. The excess EtOH was then removed by rotary evaporation or freeze-drying and the final EtOH content was thereafter adjusted as required.

2) GLP-1 was first dissolved in a small amount of sterile water. A pre-made liquid mixture of PC, GDO and EtOH, where the EtOH content was about 5-10% by weight, was then added to the GLP-1/water solution. The resulting mixture was mixed by vortex mixing for 1 min.

The final compositions of the samples are given in Table 4 below. Several purity levels of GDO and both soy and egg phosphatidylcholine (PC) were used.

TABLE 4

Compositions containing GLP-1

| Formulation | GLP-1/ wt % | PC/ wt % | GDO1/ wt % | GDO2/ wt % | GDO3/ wt % | EtOH/ wt % | $H_2O$/ wt % |
|---|---|---|---|---|---|---|---|
| A | 0.5 | 44.75 | 44.75 | — | — | 10 | — |
| B | 0.5 | 44.75 | — | 44.75 | — | 10 | — |
| C | 0.5 | 44.75 | — | — | 44.75 | 10 | — |
| D | 1.0 | 44.5 | — | — | 44.5 | 10 | — |
| E | 1.0 | 46 | — | — | 46 | 7 | — |
| F | 1.0 | 47 | — | — | 47 | 5 | — |
| G | 2.0 | 44 | — | — | 44 | 10 | — |
| H | 2.0 | 45.5 | — | — | 45.5 | 7 | — |
| I | 2.0 | 46.5 | — | — | 46.5 | 5 | — |
| J | 3.0 | 46 | — | — | 46 | 5 | — |
| K | 0.5 | 35.775 | — | — | 43.725 | 10 | 10 |
| L | 1.0 | 35.55 | — | — | 43.45 | 10 | 10 |
| M | 2.0 | 37.35 | — | — | 45.65 | 5 | 10 |
| N | 2.0 | 32.85 | — | — | 40.15 | 10 | 15 |
| O | 2.0 | 30.4 | — | — | 45.6 | 10 | 12 |
| P | 3.0 | 30 | — | — | 45 | 10 | 12 |
| Q | 3.0 | 31.875 | — | — | 43.125 | 10 | 12 |
| R | 3.0 | 32.4 | — | — | 39.6 | 10 | 15 |
| S | 2.0* | 46.5 | — | — | 46.5 | 5 | — |
| T | 2.0* | 32.85 | — | — | 40.15 | 10 | 15 |
| U | 2.0* | 30.4 | — | — | 45.6 | 10 | 12 | where EtOH is ethanol, PC is LIPOID S100 soybean phosphatidylcholine or LIPOID E 80 egg phosphatidylcholine (marked with *) and GDO is glycerol dioleate

TABLE 5

| GDO qualities used | | | |
|---|---|---|---|
| GDO quality (according to AC) | Monoglycerides | Diglycerides | Triglycerides |
| GDO1 | 10.9% | 87.5% | 1.4% |
| GDO2 | 4.2% | 92.1% | 3.5% |
| GDO3 | 0.5% | 95.3% | 4.0% |

Example 5

5.1 Preparation of Lipid Stock Solution

A lipid stock solution was prepared by sequentially adding SPC (1.44 g), GDO (1.44 g), P80 (0.72 g) and EtOH (0.40 g) to a glass vial followed by end-over-end rotation for 24 h. A clear and homogenous liquid lipid stock solution was obtained.

5.2 Preparation of Lipid/GLP-1 Formulation 20 mg of GLP-1 (acetate salt) was weighed into a vial and dissolved by adding 0.352 g of an aqueous solution containing 2 wt % HAc followed by vortex mixing.

To the aqueous stock solution of GLP-1 was added 1.628 g of the lipid stock solution prepared in 5.1. The resulting formulation was mixed by brief vortex mixing followed by end-over-end rotation for 1 h giving a clear, homogenous and low viscosity lipid/GLP-1 formulation.

| Composition in wt % | | | | | | |
|---|---|---|---|---|---|---|
| Formulation | GLP-1 | SPC | GDO | P80 | EtOH | HAc | Water |
| A | 1.0 | 29.3 | 29.3 | 14.7 | 8.1 | 0.35 | 17.25 |

Example 6

A lipid stock solution was prepared according to Example 5.1 with the following composition: SPC/GDO/EtOH=42.5/42.5/15 wt %. 2.52 g of this lipid stock solution was added to an aqueous solution of 30 mg of GLP-1 (acetate salt) dissolved in 0.450 g of 2 wt % HAc. The resulting formulation was mixed by brief vortex mixing followed by end-over-end rotation for 1 h giving a clear, homogenous and low viscosity lipid/GLP-1 formulation.

| Composition in wt % | | | | | |
|---|---|---|---|---|---|
| Formulation | GLP-1 | SPC | GDO | EtOH | HAc | Water |
| B | 1.0 | 35.7 | 35.7 | 12.6 | 0.3 | 14.7 |

Example 7

A lipid stock solution was prepared according to Example 5.1 with the following composition: SPC/GDO/P80/EtOH=35/35/20/10 wt %. 0.83 g of this lipid stock solution was added to 3 different vials containing 10 mg of GLP-1 (acetate salt) dissolved in 0.160 g of aqueous solutions containing 2 wt % HAc and 0.1 wt % Asc or 2 wt % HAc, 0.1 wt % Asc and 0.1 wt % glycine or 2 wt % HAc, 0.1 wt % Asc and 0.02 wt % EDTA (disodium salt). The resulting formulations were mixed by brief vortex mixing followed by end-over-end rotation for 1 h giving clear, homogenous and low viscosity lipid/GLP-1 formulations.

| Composition in wt % | | | | | | | | | |
|---|---|---|---|---|---|---|---|---|---|
| Formulation | GLP-1 | SPC | GDO | P80 | EtOH | HAc | Asc | Glycine | EDTA | Water |
| C | 1.0 | 29.05 | 29.05 | 16.6 | 8.3 | 0.32 | 0.02 | — | — | 15.66 |
| D | 1.0 | 29.05 | 29.05 | 16.6 | 8.3 | 0.32 | 0.02 | 0.02 | — | 15.64 |
| E | 1.0 | 29.05 | 29.05 | 16.6 | 8.3 | 0.32 | 0.02 | — | 0.003 | 15.657 |

Example 8

Lipid stock solutions were prepared according to Example 5.1 with compositions as given in the table below. The respective lipid stock solution was added to GLP-1 powder in glass vials according to the compositions indicated in the table below. The resulting formulations were mixed by shaking the vials by hand resulting in GLP-1 powder suspended in the liquid lipid formulations. The formulations were injected (syringe 23G) into excess saline (0.9% wt/v NaCl) resulting in the formation of nearly spherical depots encapsulating the suspended GLP-1.

| Composition in wt % | | | | | | | | |
|---|---|---|---|---|---|---|---|---|
| Formulation | GLP-1 | SPC or EPC* | GDO | α-Tocopherol | EtOH | PG | BzOH | BzB | NMP |
| F | 1.0 | 44.55 | 44.55 | — | 9.9 | — | — | — | — |
| G | 1.0 | 44.55* | 44.55 | — | 9.9 | — | — | — | — |
| H | 2.0 | 44.1 | 44.1 | — | 9.8 | — | — | — | — |
| I | 2.0 | 44.1 | 44.1 | — | — | 9.8 | — | — | — |
| J | 2.0 | 45.57 | 45.57 | — | 4.9 | — | 1.96 | — | — |
| K | 2.0 | 45.57* | 45.57 | — | 4.9 | — | 1.96 | — | — |
| L | 2.0 | 45.57 | 45.57 | — | 4.9 | — | — | 1.96 | — |
| M | 2.0 | 44.1 | 44.1 | — | 4.9 | — | 4.9 | — | — |

-continued

| Formulation | GLP-1 | SPC or EPC* | GDO | α-Tocopherol | EtOH | PG | BzOH | BzB | NMP |
|---|---|---|---|---|---|---|---|---|---|
| N | 2.0 | 44.1 | 44.1 | — | 4.9 | — | — | 4.9 | — |
| O | 1.0 | 44.55 | 44.55 | — | — | 6.93 | 2.97 | — | — |
| P | 1.0 | 41.43 | 50.64 | — | 6.93 | — | — | — | — |
| Q | 1.0 | 47.0 | 47.0 | — | 5.0 | — | — | — | — |
| R | 1.0 | 44.6 | 44.6 | — | 4.9 | — | — | — | 4.9 |
| S | 2.0 | 45 | 45 | — | 4.0 | — | — | — | 4.0 |
| T | 2.0 | 35.24 | — | 52.86 | 9.9 | — | — | — | — |
| U | 2.0 | 34.46 | — | 51.68 | 9.9 | — | 1.96 | — | — |
| V | 2.0 | 25.84 | — | 60.3 | 9.9 | — | 1.96 | — | — |

Composition in wt %

Example 9

A lipid stock solution was prepared according to Example 5.1 with the following composition: SPC/GDO/P80/EtOH=37.5/37.5/15/10 wt %. 0.83 g of this lipid stock solution was added to a vial containing 10 mg of GLP-1 (acetate salt) dissolved in 0.160 g of aqueous solution containing 2 wt % HAc. The resulting formulation was mixed by brief vortex mixing followed by end-over-end rotation for 1 h giving a clear, homogenous and low viscosity lipid/GLP-1 formulation.

| Formulation | GLP-1 | SPC | GDO | P80 | EtOH | HAc | Water |
|---|---|---|---|---|---|---|---|
| X | 1.0 | 31.13 | 31.13 | 12.45 | 8.3 | 0.32 | 15.68 |

Composition in wt %

Example 10

A lipid stock solution was prepared according to Example 5.1 with the composition SPC/GDO/EtOH=46/46/8 wt %. GLP-1 (20 mg/mL) was dissolved in aqueous solutions (pH was adjusted with HCl(aq) or NaOH(aq) as required to dissolve GLP-1) with compositions given in the table below. Small volumes (100 μL) of the aqueous GLP-1 solutions were added to glass vials followed by rapid freezing at −85° C. The vials were then transferred to a freeze-dryer and lyophilized. To the resulting powders was added 100-200 mg of the lipid stock solution followed by vortex mixing. The GLP-1 containing powders were thus suspended in the liquid lipid formulation (10-20 mg GLP-1/g formulation). The formulations were injected (syringe 23G) into excess saline (0.9% wt/v NaCl) resulting in the formation of nearly spherical depots encapsulating the suspended GLP-1 powder.

| Aq. solution | Sucrose | Trehalose | Lactose | Glycine | Citrate* | Glutamate | Methionine | P80 | F68 |
|---|---|---|---|---|---|---|---|---|---|
| 1 | 40 | — | — | 20 | — | — | — | — | — |
| 2 | 40 | — | — | — | — | 20 | — | — | — |
| 3 | 40 | — | — | — | — | — | 20 | — | — |
| 4 | 40 | — | — | — | 20 | — | — | 1 | — |
| 5 | 40 | — | — | — | 20 | — | — | — | 1 |
| 6 | 20 | — | — | — | 20 | 20 | — | — | 1 |
| 7 | — | 40 | — | 20 | — | — | — | — | — |
| 8 | — | 40 | — | — | 20 | 20 | — | — | — |
| 9 | — | 40 | — | — | 40 | — | — | 1 | — |
| 10 | — | 40 | — | — | — | 20 | — | — | 1 |
| 11 | — | 20 | — | 20 | 20 | — | — | — | 1 |
| 12 | — | — | 40 | 20 | 20 | — | — | — | — |
| 13 | — | — | 40 | — | — | 20 | — | 1 | — |
| 14 | — | — | 40 | — | — | — | 20 | — | 1 |
| 15 | — | — | 20 | — | 20 | 20 | — | — | 1 |

Composition in mg/mL

*(di sodium salt)

Example 11

A lipid stock solution was prepared according to Example 5.1 with the composition SPC/GDO/EtOH=46/46/8 wt %. GLP-1 (1 mg/mL) was dissolved in 30 mL of an aqueous solution containing sucrose (2 mg/mL), glycine (1 mg/mL), citrate (1 mg/mL) and F68 (0.05 mg/mL) (pH was adjusted with HCl(aq) as required to dissolve GLP-1). The aqueous GLP-1 solution was spray-dried (BÜCHI Mini Spray-dryer) to form a GLP-1 containing powder. To the resulting powder (50 mg) was added 450 mg of the lipid stock solution followed by vortex mixing. The GLP-1 containing powder was thus suspended in the liquid lipid formulation. The formulation was injected (syringe 23G) into excess saline (0.9% wt/v NaCl) resulting in the formation of a nearly spherical depot encapsulating the suspended GLP-1 powder.

Example 12

A lipid stock solution was prepared according to Example 5.1 with the following composition: SPC/GDO/P80/EtOH=44.2/44.2/1.6/10 wt %. 0.99 g of this lipid stock solution was added to a vial containing 10 mg of GLP-1 powder. The resulting formulation was mixed by shaking the vial by hand resulting in the GLP-1 powder being suspended in the liquid lipid formulation. The formulation was injected (syringe 23G) into excess saline (0.9% wt/v NaCl) resulting in the formation of a nearly spherical depot encapsulating the suspended GLP-1.

Example 13

13.1 Animal Studies—General Procedure

On the first day of the study, the rats (male Sprague-Dawley rats) were weighed and prepared for the experiment by insertion of a venous catheter according to standard procedures. Briefly, the rats were anesthetized with enfluran and buprinorphin. A silicon catheter was inserted in the jugular vein, fixated and tunneled beneath the skin to the dorsal part of the neck, where it was externalized for sampling of blood. The rats were allowed 48 hrs of recovery before dosing.

The catheter was rinsed with 0.9% NaCl with 50 IU/mL Heparin once per day. After recovery, the animals were weighed and Formulation B (Example 6) and Formulation F (Example 8) were injected subcutaneously (n=6 per formulation) under light anaesthesia at a dose of 10 mg GLP-1/kg and dose volume of 1 mL/kg. A Placebo formulation comprising SPC/GDO/EtOH=45/45/10 wt % was injected (n=6) as reference at a dose volume of 1 mL/kg. The animals were allowed free access to water and food after dosing.

13.2 Sampling

Blood samples were collected pre-dose, 1 hr, 3 hrs, 6 hrs, 1 day, 2 days, 7 days, 14 days, 21 days, and 28 days after dosing. Blood samples of 0.4 mL blood were collected in ice-cooled EDTA-treated test tubes. A commercial DPP-IV inhibitor was added in the test tubes. After each sampling, sterile 0.9% NaCl (with 10 mM EDTA) for injection was given to the rats through the catheter to compensate for the lost blood volume.

13.3 Bioanalysis

The samples were stored at <−80° C. prior to analysis. GLP-1 concentration in the EDTA plasma samples was measured by a commercial ELISA (Glucagon-Like Peptide-1 (Active) ELISA Kit, Cat. #EGLP-35K, Linco Research).

13.4 Results

FIG. 1 displays the PK profiles. It can be seen that the GLP-1 plasma levels were significantly elevated compared to Placebo for a period of 28 days. Importantly, there was no lag phase of the release and stable plateau plasma GLP-1 levels were reached within 2 days post-injection for both formulations. The duration of the GLP-1 depot formulations is remarkable considering the very short plasma half-life (<5 min) of the peptide.

Example 14

A lipid stock solution was prepared according to Example 5.1 with the following composition: SPC/GDO/DOPG/EtOH=44/46/2/8 wt %. The lipid stock solution (0.49 g) was added to GLP-1 powder (10 mg) in a glass vial. The resulting formulation was mixed by shaking the vial by hand resulting in the GLP-1 powder being suspended in the liquid lipid formulation. The formulation was injected (syringe 23G) into excess saline (0.9% wt/v NaCl) resulting in the formation of a nearly spherical depot encapsulating the suspended GLP-1.

The invention claimed is:

1. A formulation comprising a low viscosity mixture of:
   a) at least one neutral diacyl lipid and/or a tocopherol;
   b) at least one phospholipid;
   c) at least one biocompatible organic solvent comprising ethanol; and
   d) 0.02 to 12 wt. % of at least one GLP-1 receptor agonist or antagonist:
   wherein the formulation forms at least one liquid crystalline phase structure upon contact with an aqueous fluid;
   wherein the ratio of a):b) is in the range 40:60 to 70:30 by weight.

2. The formulation of claim 1, comprising a low viscosity mixture of:
   a) wherein the at least one neutral diacyl lipid is selected from at least one diacyl glycerol;
   b) wherein the at least one phospholipid is selected from at least one phosphatidyl choline;
   c) wherein the at least one biocompatible organic solvent comprising ethanol is selected from at least one oxygen containing organic solvent; and
   d) 0.02 to 12 wt. % of at least one GLP-1 receptor agonist or antagonist;
   wherein the formulation forms at least one liquid crystalline phase structure upon contact with an aqueous fluid;
   wherein the ratio of a):b) is in the range 40:60 to 70:30 by weight.

3. The formulation of claim 1, wherein component a) comprises glycerol dioleate.

4. The formulation of claim 1, wherein component b) comprises soy phosphatidyl choline.

5. The formulation of claim 1, wherein said formulation comprises at least one GLP-1 receptor agonist or antagonist selected from the group consisting of native GLP-1, Liraglutide, TH-0318, Exenatide and AVE-010.

6. The formulation of claim 1, wherein said formulation further comprises at least one polyethyleneoxide fragmentation agent.

7. A pre-loaded device with a measured dose of a formulation comprising a low-viscosity mixture of:
   a) at least one neutral diacyl lipid and/or a tocopherol;
   b) at least one phospholipid;
   c) at least one biocompatible organic solvent comprising ethanol; and
   d) 0.02 to 12 wt. % of at least one GLP-1 receptor agonist or antagonist;
   wherein the ratio of a):b) is in the range 40:60 to 70:30 by weight.

8. The device of claim 7, wherein the dose comprises a single dose of 0.05 to 250 mg of at least one GLP-1 receptor agonist or antagonist.

9. The device of claim 7, wherein the device contains a total volume for administration of no more than 5 ml.

10. A kit for the administration of at least one GLP-1 receptor agonist or antagonist, said kit comprising a measured dose of a formulation comprising a low-viscosity mixture of:
    a) at least one diacyl glycerol:
    b) at least one phosphatidyl choline;
    c) at least one oxygen containing organic solvent comprising ethanol; and
    d) 0.02 to 12 wt. % of at least one GLP-1 receptor agonist or antagonist;
    wherein the ratio of a):b) is in the range 40:60 to 70:30 by weight.

11. The kit of claim 10, wherein the kit further comprises a needle smaller than 20 gauge.

12. The kit of claim 10, wherein the dose comprises a single dose of 0.05 to 250 mg of at least one GLP-1 receptor agonist or antagonist.

13. The kit of claim 10, wherein the formulation comprises at least one GLP-1 receptor agonist or antagonist selected from the group consisting of native GLP-1, Liraglutide, TH-0318, Exenatide and AVE-010 at about 0.05 to 250 mg.

14. The kit of claim 10, wherein the kit further comprises instructions for administering the formulation intramuscularly or subcutaneously.

15. A kit for the administration of at least one GLP-1 receptor agonist or antagonist wherein the said kit is a two-component kit comprising:
- i) a first component containing a low viscosity mixture of a) at least one diacyl glycerol, b) at least one phosphatidyl choline and c) at least one oxygen containing organic solvent comprising ethanol; and
- ii) a second component containing 0.02 to 12 wt. % of at least one GLP-1 receptor agonist or antagonist, wherein the ratio of a):b) is in the range 40:60 to 70:30 by weight.

* * * * *

```
                       SEQUENCE LISTING

<160> NUMBER OF SEQ ID NOS: 4

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 30
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```